(12) United States Patent
Goldston et al.

(10) Patent No.: US 10,449,413 B2
(45) Date of Patent: Oct. 22, 2019

(54) EXERCISE DEVICES AND METHODS WITH RETRACTABLE CORDS

(71) Applicants: Mark R. Goldston, Beverly Hills, CA (US); Sharon Kripke, Toledo, OH (US); Shari Konikoff, Beachwood, OH (US); John P. Goodworth, Medina, OH (US)

(72) Inventors: Mark R. Goldston, Beverly Hills, CA (US); Sharon Kripke, Toledo, OH (US); Shari Konikoff, Beachwood, OH (US); John P. Goodworth, Medina, OH (US)

( * ) Notice: Subject to any disclaimer, the term of this patent is extended or adjusted under 35 U.S.C. 154(b) by 387 days.

(21) Appl. No.: 15/230,290

(22) Filed: Aug. 5, 2016

(65) Prior Publication Data

US 2017/0036063 A1 Feb. 9, 2017

Related U.S. Application Data

(60) Provisional application No. 62/202,694, filed on Aug. 7, 2015.

(51) Int. Cl.
*A63B 23/18* (2006.01)
*A63B 21/00* (2006.01)
(Continued)

(52) U.S. Cl.
CPC ........ *A63B 23/18* (2013.01); *A63B 21/00043* (2013.01); *A63B 21/00069* (2013.01);
(Continued)

(58) Field of Classification Search
CPC . A63B 23/18; A63B 21/025; A63B 21/00043; A63B 23/1245; A63B 23/1281; A63B 23/1209; A63B 23/03541; A63B 21/1618; A63B 71/0622; A63B 21/153; A63B 21/169; A63B 21/00069; A63B 21/4035; A63B 21/16; A63B 2022/0092; A63B 24/0087; A63B 2208/0228; A63B 21/028; A63B 21/1627; A63B 21/1636; A63B 2071/065; A63B 23/03508; A63B 2208/0233; A63B 2208/0238;
(Continued)

(56) References Cited

U.S. PATENT DOCUMENTS

| | | | | |
|---|---|---|---|---|
| 5,833,587 A | * | 11/1998 | Strong | A63B 21/154 482/123 |
| 6,099,447 A | * | 8/2000 | Ramsaroop | A63B 21/153 482/107 |

(Continued)

*Primary Examiner* — Garrett K Atkinson
(74) *Attorney, Agent, or Firm* — Foley & Lardner LLP

(57) ABSTRACT

An exercise apparatus includes a first cord, a second cord, and an adjustment mechanism. The first cord is pullable from and retractable around a first pulley. The second cord is pullable from and retractable around a second pulley. The adjustment mechanism allows for adjusting a pull-out tension provided by the first cord independently of a retraction tension provided by the first cord. The pull-out tension provided by the first cord is a tension provided by the first cord when the first cord is pulled from the first pulley. The retraction tension provided by the first cord is a tension provided by the first cord when the first cord is retracted around the first pulley.

20 Claims, 20 Drawing Sheets

(51) Int. Cl.
*A63B 21/16* (2006.01)
*A63B 71/06* (2006.01)
*A63B 23/035* (2006.01)
*A63B 23/12* (2006.01)
*G06F 19/00* (2018.01)
*A63B 21/02* (2006.01)
*A63B 21/055* (2006.01)
*A63B 71/00* (2006.01)
*A63B 24/00* (2006.01)
*A63B 22/00* (2006.01)

(52) U.S. Cl.
CPC .......... *A63B 21/025* (2013.01); *A63B 21/153* (2013.01); *A63B 21/16* (2013.01); *A63B 21/169* (2015.10); *A63B 21/1618* (2013.01); *A63B 21/4035* (2015.10); *A63B 23/03541* (2013.01); *A63B 23/1209* (2013.01); *A63B 23/1245* (2013.01); *A63B 23/1281* (2013.01); *A63B 71/0622* (2013.01); *G06F 19/3481* (2013.01); *A63B 21/028* (2013.01); *A63B 21/0552* (2013.01); *A63B 21/154* (2013.01); *A63B 21/1627* (2013.01); *A63B 21/1636* (2013.01); *A63B 21/4009* (2015.10); *A63B 21/4043* (2015.10); *A63B 23/03508* (2013.01); *A63B 24/0087* (2013.01); *A63B 2022/0092* (2013.01); *A63B 2071/0018* (2013.01); *A63B 2071/065* (2013.01); *A63B 2071/0625* (2013.01); *A63B 2071/0694* (2013.01); *A63B 2208/0204* (2013.01); *A63B 2208/0228* (2013.01); *A63B 2208/0233* (2013.01); *A63B 2208/0238* (2013.01); *A63B 2220/51* (2013.01); *A63B 2220/56* (2013.01); *A63B 2225/055* (2013.01); *A63B 2225/50* (2013.01); *A63B 2230/207* (2013.01); *A63B 2230/433* (2013.01); *A63B 2230/436* (2013.01)

(58) Field of Classification Search
CPC ........ A63B 2071/0625; A63B 21/4043; A63B 2230/207; A63B 2225/50; A63B 2225/055; A63B 2220/56; A63B 2220/51; A63B 2208/0204; A63B 2071/0694; A63B 2071/0018; A63B 2230/436; A63B 2230/433; A63B 21/0552; A63B 21/154; A63B 21/4009; G06F 19/3481
See application file for complete search history.

(56) References Cited

U.S. PATENT DOCUMENTS

| | | | | |
|---|---|---|---|---|
| 6,837,835 | B2* | 1/2005 | Huang | A63B 21/0552 482/122 |
| 6,837,836 | B2* | 1/2005 | Huang | A63B 21/0552 482/122 |
| 7,344,487 | B2* | 3/2008 | Carter | A63B 21/0552 482/142 |
| 7,674,216 | B1* | 3/2010 | Bolling | A63B 23/03516 446/220 |
| 7,955,239 | B2* | 6/2011 | Wojtkiw | A63B 21/04 482/129 |
| 9,700,751 | B2* | 7/2017 | Verdi | A63B 21/4019 |
| 9,744,397 | B2* | 8/2017 | Pagano | A63B 22/18 |

* cited by examiner

FLOOR SEATED

FLOOR SEATED

CHAIR SEATED

WHEELCHAIR
SEATED

STANDING WITH
TELESCOPING STAND

HOSPITAL
BED

WITH ADJUSTABLE GUIDE
TRACKS AND HANDLES

WITH ADJUSTABLE GUIDE
TRACKS AND HANDLES

EXERCISE DEVICES AND METHODS WITH RETRACTABLE CORDS

CROSS-REFERENCE TO RELATED PATENT APPLICATIONS

This application claims priority from U.S. Provisional Patent Application Ser. No. 62/202,694, filed Aug. 7, 2015, the entire contents of which are incorporated by reference herein.

FIELD

Various embodiments in the present disclosure relate generally to the field of exercise devices and methods. More specifically, various embodiments relate to an exercise device and method for improving posture, oxygen intake, and breathing efficiency.

BACKGROUND

Proper posture and breathing are generally considered important for health and wellness. Some individuals, such as the injured and individuals suffering from respiratory diseases like asthma, may have trouble breathing efficiently. Insufficiently engaging the diaphragm can result in inefficient breaths that take in too little oxygen and expel too little carbon dioxide. Incorrect posture can lead to long term problems for a body, such as pain in various locations, poor circulation, and fatigue.

SUMMARY OF THE DISCLOSURE

An exercise apparatus in accordance with various embodiments includes a first cord, a second cord, and an adjustment mechanism. The first cord is pullable from and retractable around a first pulley. The second cord is pullable from and retractable around a second pulley. The adjustment mechanism allows for adjusting a pull-out tension provided by the first cord independently of a retraction tension provided by the first cord. The pull-out tension provided by the first cord is a tension provided by the first cord when the first cord is pulled from the first pulley. The retraction tension provided by the first cord is a tension provided by the first cord when the first cord is retracted around the first pulley.

In various embodiments, the adjustment mechanism includes a member that is shaped to provide a resistance against movement of the first pulley when the first pulley rotates in a first direction and to permit movement of the first pulley when the first pulley rotates in an opposite direction from the first direction. In various embodiments, the first pulley is configured to rotate in the first direction when the first cord is pulled from the first pulley, and is configured to rotate in the opposite direction when the first cord is retracted around the first pulley.

In various embodiments, the exercise apparatus further includes a second adjustment mechanism for adjusting a pull-out tension provided by the second cord independently of a retraction tension provided by the second cord. The pull-out tension provided by the second cord is a tension provided by the second cord when the second cord is pulled from the second pulley, and the retraction tension provided by the second cord is a tension provided by the second cord when the second cord is retracted around the second pulley. In various embodiments, the adjustment mechanism includes a knob for adjusting a resistance to be applied to the first pulley against rotation of the first pulley in a first direction independent of any adjustment of freedom of movement of the first pulley in an opposite direction from the first direction.

In various embodiments, the exercise apparatus further includes a shaft, and the first pulley and the second pulley are both positioned around the shaft. In some embodiments, the exercise apparatus further includes a first shaft and a second shaft separate from the first shaft, and the first pulley is positioned around the first shaft, and the second pulley is positioned around the second shaft.

In various embodiments, the exercise apparatus further includes a main body for housing the first pulley and the second pulley, where the main body includes a first opening through which the first cord is moveable and a second opening through which the second cord is moveable. In some embodiments, the main body is in the shape of a sphere and the first opening is on an opposite side of the sphere from the second opening. In some embodiments, the main body is in the shape of a sphere and the first opening is entirely within a same hemisphere of the sphere as the second opening. In some embodiments, the main body further includes a threaded opening for attachment of the main body to a mounting device. Also, in some embodiments, the exercise apparatus further includes a first handle attached to the first cord, and a second handle attached to the second cord.

An exercise apparatus assembly in accordance with an embodiment includes an exercise apparatus and a mounting device. The exercise apparatus includes a first cord, a second cord, and an adjustment mechanism. The first cord is pullable from and retractable around a first pulley. The second cord is pullable from and retractable around a second pulley. The adjustment mechanism allows for adjusting a pull-out tension provided by the first cord independently of a retraction tension provided by the first cord. The pull-out tension provided by the first cord is a tension provided by the first cord when the first cord is pulled from the first pulley. The retraction tension provided by the first cord is a tension provided by the first cord when the first cord is retracted around the first pulley. The exercise apparatus is configured such that the exercise apparatus is mountable on and removable from the mounting device.

In various embodiments, the mounting device includes a first coupling member for connecting the exercise apparatus to the mounting device and a second coupling member for mounting the mounting device on an object. In various embodiments, the mounting device further includes an adjustment member that is moveable to hold the object between the adjustment member and the second coupling member. Also, in various embodiments, the adjustment member is located on an opposite side of the second coupling member from the first coupling member. In some embodiments, the mounting device comprises a belt for wearing by a user. Also, in some embodiments, the mounting device comprises a suction cup for providing suction to an object.

A method for using an exercise apparatus in accordance with an embodiment includes moving an adjustment mechanism to adjust a pull-out tension provided by a first cord of the exercise apparatus independently of a retraction tension provided by the first cord. The pull-out tension is a tension provided by the first cord when the first cord is pulled from a first pulley, and the retraction tension is a tension provided by the first cord when the first cord is retracted around the first pulley. In various embodiments, the method further includes pulling the first cord and a second cord of the exercise apparatus at a same time and each in an arc motion. In some embodiments, the method further includes attaching the exercise apparatus to a door using a plurality of clips that slide on the door.

BRIEF DESCRIPTION OF THE DRAWINGS

Features, aspects, and advantages of the present invention will become apparent from the following description, appended claims, and the accompanying exemplary embodiments shown in the drawings, which are briefly described below.

DETAILED DESCRIPTION OF EXEMPLARY EMBODIMENTS

The following detailed description is now directed to certain embodiments of the disclosure. In this description, reference is made to the drawings wherein like parts are designated with like numerals throughout the description and the drawings.

Figure 1:
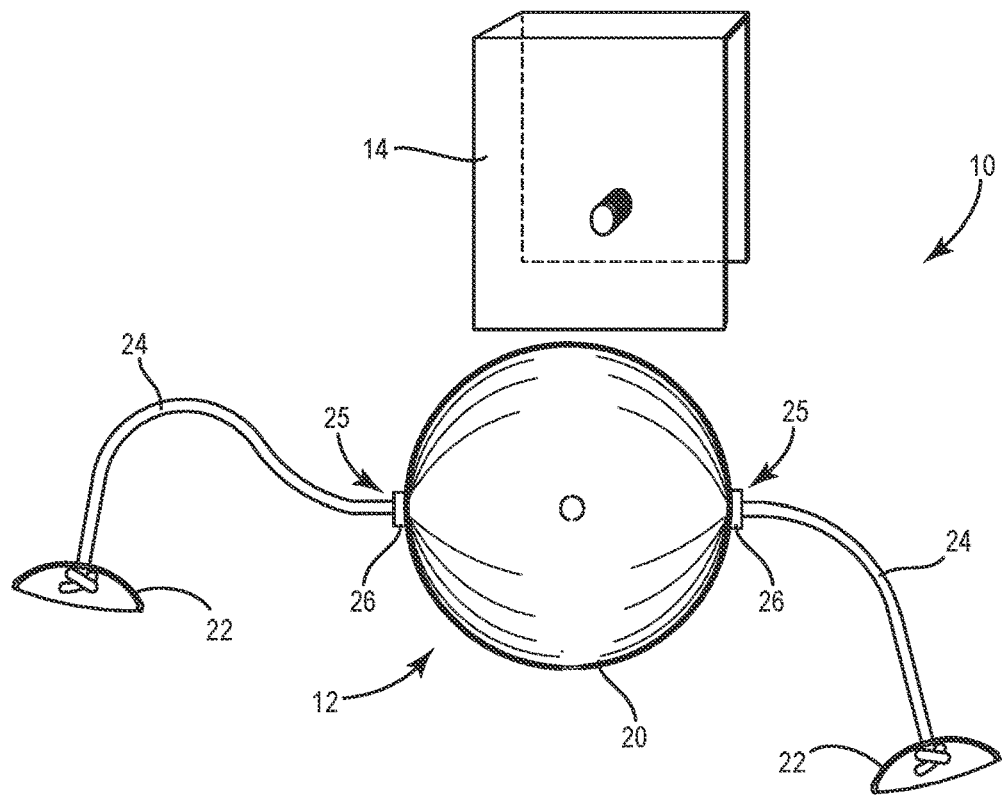
FIG. 1 is a front perspective view of an exercise apparatus assembly including an exercise apparatus and a mounting device, according to an exemplary embodiment.

Referring to FIG. 1, an exercise apparatus assembly 10 is shown according to an exemplary embodiment. The exercise apparatus assembly 10 includes an exercise device or exercise apparatus 12 and a mounting device 14 that is a stabilization device for the exercise apparatus 12. In various embodiments, the exercise apparatus 12 is configured to be engaged by the hands of a user and provides a tensile force resisting outward movement of the hands throughout a natural range of motion of the hands. In various embodiments, the mounting device 14 is configured to couple the exercise apparatus 12 to a relatively stationary base object. As described in more detail below, the stationary base object may be any object that remains relatively stationary as the user's hands move including, but not limited to, a table, a door, a stand, or the user's own body.

Referring to FIG. 1, according to an exemplary embodiment, the exercise apparatus 12 includes a main body 20 and a pair of user interface members, shown as handles 22 that are coupled to the main body 20 with retractable cords 24, such as cables, wires, ropes, strings, or the like, that extend through openings 25 in the main body 20. Wear bearings 26 are provided in the openings 25. In various embodiments, the main body 20 has internal mechanisms to apply a tension on each of the cords 24 to pull each of the handles 22 towards the main body 20. A user may grasp the handles 22 and apply an outward force to the handles 22 to extend the cords 24 as they move their hands apart from one another and away from the main body 20. As the user's arms relax and the outward force applied to the handles 22 is reduced below the tension applied by the internal mechanisms of the exercise apparatus 12, the tension retracts the cords 24 and pulls the handles 22 and the user's hands back towards the main body 20. In various embodiments, the exercise apparatus 12 allows a user's hands to follow an arc motion that orients the user's body to improve posture and respiration efficiency. According to an exemplary embodiment, the arc motion orients the shoulders rearward and orients the chest outward and upward, which enables the lungs to fill with air while engaging the diaphragm. The exercise apparatus 12 can be used with a single hand engaging one of the handles 22 or with both hands simultaneously. In various embodiments, the main body 20 is shaped as a sphere and the openings 25 are positioned on opposite sides of the sphere from each other.

In some embodiments, the handles 22 are configured to be interchangeable. For example, several different sized handles and/or shaped handles may be provided for the exercise apparatus 12 to accommodate users with different hand sizes. In some embodiments, the handles 22 are formed from a relatively rigid material, such as a rigid polymer, or the like. In some embodiments, the handles 22 are formed completely or partially from a resilient material. Forming the handles 22 from a resilient material allows the user to squeeze the handles 22 during the exercise, adding an additional method of exercising. In some embodiments, one or both of the handles 22 includes a pulse meter inside a receptacle in the handle 22, such as a hollow, an opening, or the like, configured to receive a fingertip that touches the pulse meter. In various embodiments, the pulse meter is activated automatically by inserting a finger into the receptacle in the handle 22. In some embodiments, one or both of the handles 22 includes a pulse-blood oxygen level meter inside a receptacle in the handle 22, such as a hollow, an opening, or the like, configured to receive a fingertip that touches the pulse-blood oxygen level meter. In various embodiments, the pulse-blood oxygen level meter is activated automatically by inserting a finger into the receptacle of the handle 22. In some embodiments, the handles 22 include removable, interchangeable weights. The weights may be configured to attach to each other and/or each of the handles 22 to provide weighted resistance to a user.

In some embodiments, the cords 24 are flexible members that are able to stretch and contract. In some embodiments, the cords 24 are non-flexible members with a fixed length. In some embodiments, each of the cords 24 includes a conducting member, such as a wire, a metal trace, or the like, to conduct signals from the correspondingly attached handle 22 to the main body 20. In various embodiments, the main body 20 of the exercise apparatus 12 is shaped as a sphere with a width that is about the width of an adult human body.

Figure 2:
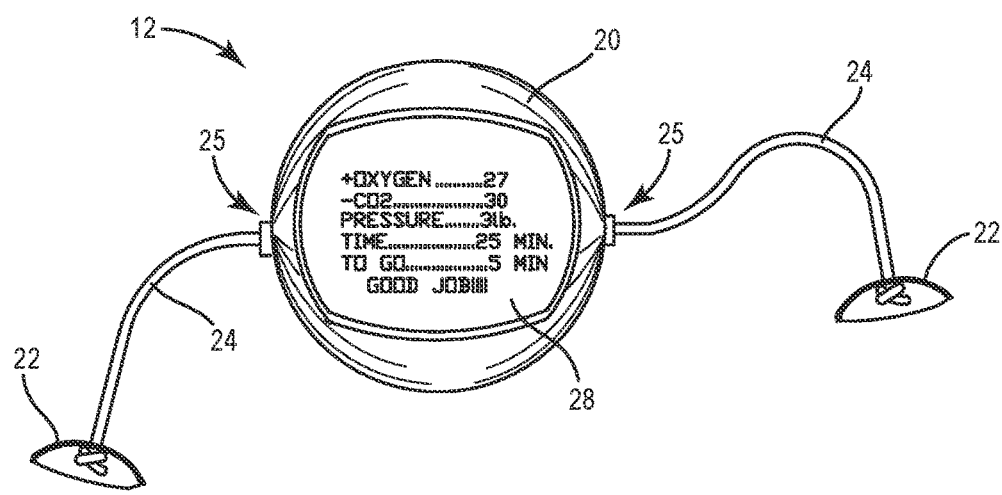
FIG. 2 is a rear perspective view of the exercise apparatus of FIG. 1, according to an exemplary embodiment.

Referring to FIG. 2, in some embodiments, the exercise apparatus 12 includes a screen 28. The screen 28 is configured to display information to the user, such as information related to the user's respiration or the like. In various embodiments, the exercise apparatus 12 is configured to track the activities of the user over a certain amount of time. According to an exemplary embodiment, the screen 28 is configured to display an elapsed time, a remaining time, an estimated amount of oxygen inhaled, an estimated amount of carbon dioxide exhaled, and the tension or pressure being applied to the handles 22 via the cords 24. In various embodiments, the screen 28 is configured to display instructions, warnings, encouragements, or other information to the user. In some embodiments, the screen is an LED screen and includes a computing device for controlling information on the LED screen. In some embodiments, the exercise apparatus 12 includes a user input device, such as a touchscreen, a keypad, a computing device in communication with the exercise apparatus 12, or the like. In some embodiments, the exercise apparatus includes an internal processing unit in communication with the screen 28 and one or more sensors, such as pulse sensors, blood oxygen level sensors, clocks, or the like. In some embodiments, the internal processing unit is in communication with sensors in the handles 22 through conducting members in the cords 24 or through wireless communication, and is configured to receive data from the sensors and to process the data to display information on the screen 28.

Figure 3:
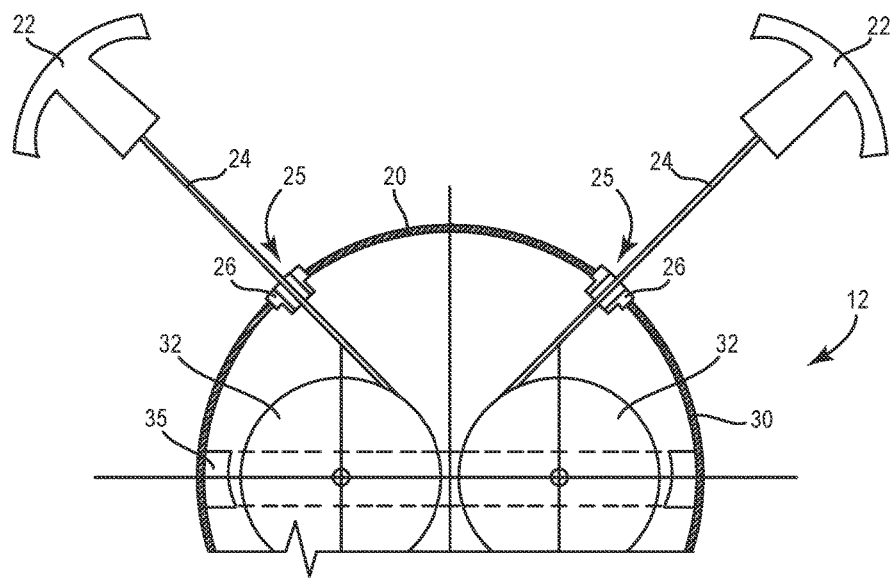
FIG. 3 is a side view of the interior of the exercise apparatus of FIG. 1, according to an exemplary embodiment.
Figure 4:
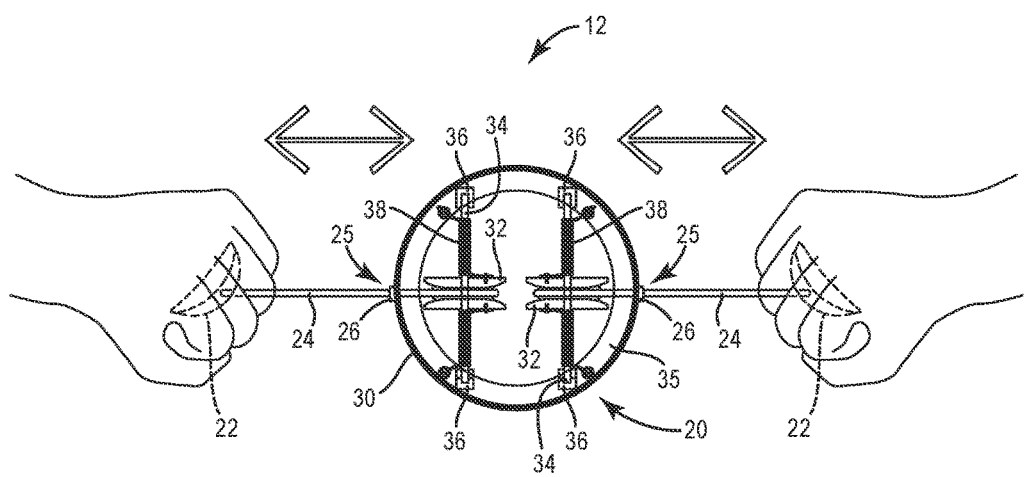
FIG. 4 is a top view of the interior of the exercise apparatus of FIG. 1, according to an exemplary embodiment.

Referring now to FIGS. 3 and 4, internal mechanisms of the exercise apparatus 12 are shown according to an exemplary embodiment. Each of the cords 24 extends through an outer housing 30 of the main body 20 through the corresponding opening 25 and wear bearing 26, and engages a corresponding pulley 32. In various embodiments, the pulleys 32 are coupled to separate parallel drive shafts 34, which are mounted to an internal frame 35 inside the outer housing 30. Bearings 36, such as needle bearings, or the like, allow the drive shafts 34 to rotate relative to the outer housing 30. In various embodiments, tension is applied to each of the cords 24 via corresponding torsion springs 38, which provide a constant, predetermined torsion resisting the rotation of the pulleys 32 in a direction corresponding to the extension of the cords 24.

Figure 5:
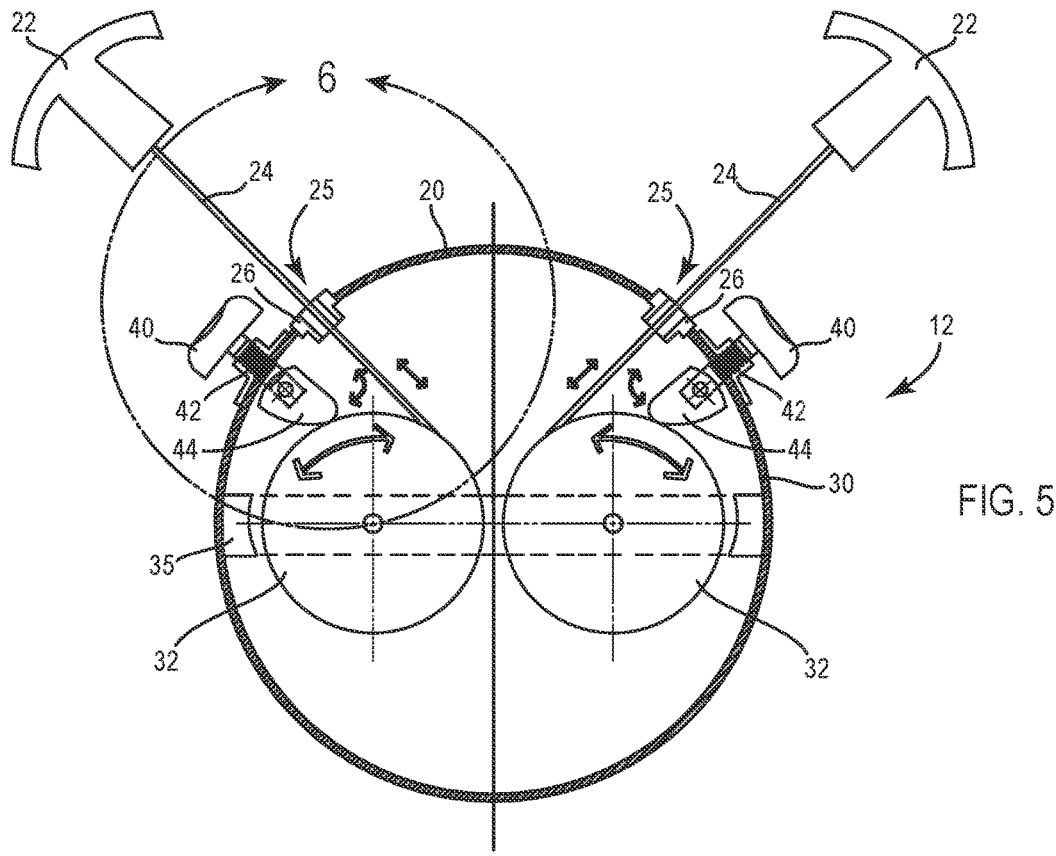
FIG. 5 is a side view of the interior of an exercise apparatus, according to an exemplary embodiment.
Figure 6:
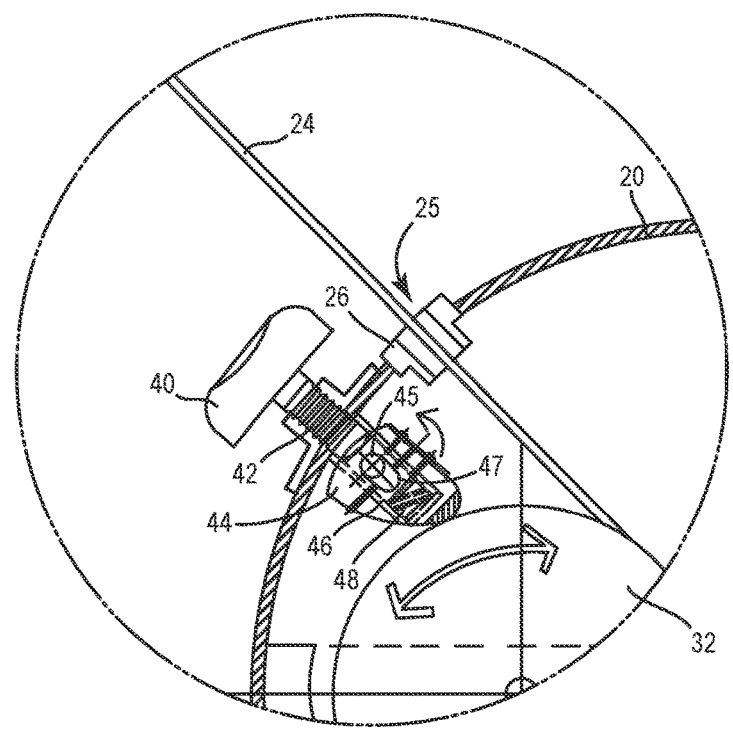
FIG. 6 is a detailed interior view of a portion of the exercise apparatus of FIG. 5.

Referring now to FIGS. 5 and 6, internal mechanisms of the exercise apparatus 12 are shown according to another exemplary embodiment to include a means for adjusting the tension or resistance applied to the pulleys 32 to resist the rotation of the pulleys 32 in a direction corresponding to the extension of the cords 24. Knobs 40 are provided, with each knob 40 corresponding to a pulley 32 to allow a user to rotate the knob 40 to rotate a threaded rod 42 to apply a resistance to the rotation of the pulley 32 with a foot member 44. The threaded rod 42 attached to a corresponding knob 40 engages the main body 20 with a threaded connection and is received by a corresponding hollow sheath 46. A biasing member, shown as a coil spring 48 is disposed between the end of the threaded rod 42 and an end of the hollow sheath 46. The coil spring 48 forces the hollow sheath 46 against the foot member 44. The foot member 44, in turn, is forced against the outside circumference of the corresponding pulley 32. The user may advance or retract the threaded rod 42 by turning the corresponding knob 40 to increase or decrease the resistance applied to the pulley 32 by the corresponding foot member 44. In various embodiments, each knob 40 with the corresponding threaded rod 42, foot member 44, hollow sheath 46, and coil spring 48 comprises an adjustment mechanism of the exercise apparatus 12 for adjusting a pull-out tension provided by the corresponding cord 24 independently of a retraction tension provided by the corresponding cord 24. The pull-out tension of each cord 24 is a tension provided by the cord 24 when the cord 24 is pulled from the corresponding pulley 32, and the retraction tension of the cord 24 is a tension provided by the cord 24 when the cord 24 is retracted around the corresponding pulley 32. With two resistance adjustment mechanisms, a user may be able to set the resistance for each pulley 32 separately, such as by using the two knobs 40. In various embodiments, each foot member 44 includes an opening 47 through which a corresponding pin 45 extends. Of course, it should be appreciated that other adjustment mechanisms for adjusting tension are possible, such as manually controlled adjustment mechanisms, electronically controlled adjustment mechanisms, or the like.

In various embodiments, the adjustment mechanism for adjusting the tension of a corresponding cord 24 includes the foot member 44, and the foot member 44 is shaped to provide a resistance against movement of the corresponding pulley 32 when the pulley 32 rotates in a first direction and to permit movement of the pulley 32 when the pulley 32 rotates in an opposite direction from the first direction. In various embodiments, the first direction is a direction of rotation of the pulley 32 when the corresponding cord is pulled from the pulley 32, and the opposite direction is a direction of rotation of the pulley 32 when the corresponding cord is retracted around the pulley 32. In some embodiments, each cord 24 is configured to have an initial tension that is symmetrical for both pulling-out and retraction of the cord. For example, there may be an initial bi-directional tension that is equal for both pulling-out and retraction for each cord 24. In various embodiments, the adjustment mechanism corresponding to each cord 24 allows for increasing the pull-out tension of the cord 24 while leaving the retraction tension of the cord 24 at the initial value. In various embodiments, the knob 40 of each adjustment mechanism allows for adjusting a resistance to be applied to the corresponding pulley 32 against rotation of the pulley 32 in a first direction independent of any adjustment of freedom of movement of the pulley 32 in an opposite direction from the first direction.

In various embodiments, the main body 20 is a spherical shape and the openings 25 are entirely within a same hemisphere of the sphere as each other, as shown in FIG. 5. In some embodiments, the sphere for the main body 20 has a diameter of 5 inches. Of course, other sizes could be used for the sphere. For example, the sphere may have a diameter of 3 inches, 4 inches, or any other desired size. In various embodiments, each cord 24 is between 6 and 16 feet in length, although other desired lengths could also be used. In various embodiments, each cord 24 provides 1 pound of resistance as an initial value and the resistance for pulling out each cord 24 is adjustable independently of any resistance for retraction of the cord 24.

Figure 7:
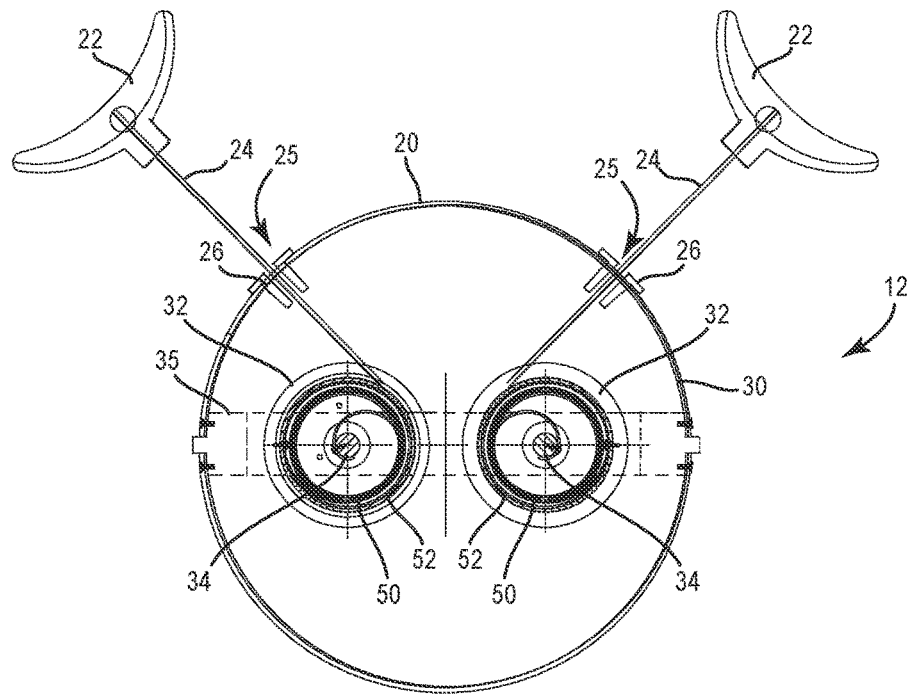
FIG. 7 is a side view of the interior of an exercise apparatus, according to an exemplary embodiment.
Figure 8:
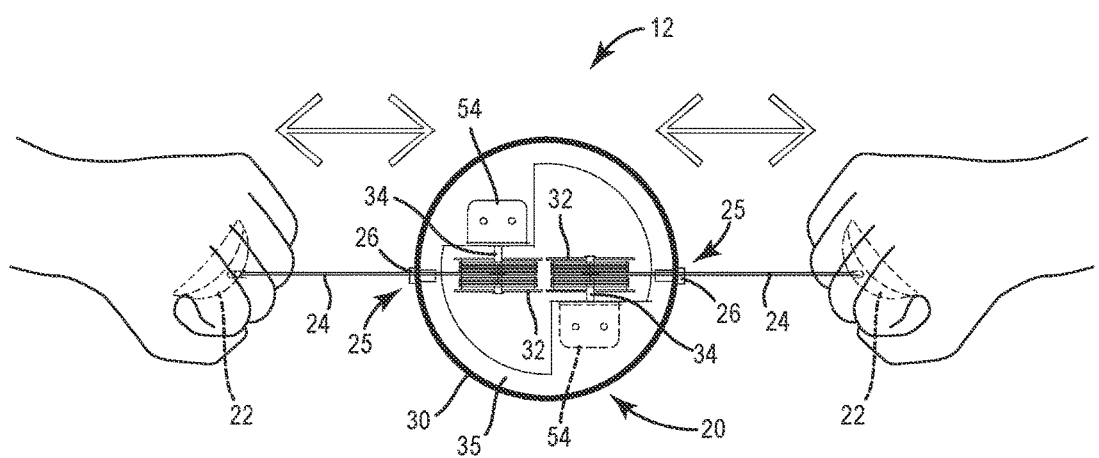
FIG. 8 is a top view of the interior of the exercise apparatus of FIG. 7.

Referring now to FIGS. 7 and 8, internal mechanisms of the exercise apparatus 12 are shown according to another exemplary embodiment. Each of the cords 24 extends through the outer housing 30 of the main body 20 through the corresponding opening 25 and engages the corresponding pulley 32. The pulleys 32 are coupled to separate parallel drive shafts 34. Tension is applied to the cords 24 via corresponding clock springs 50, which provide a constant, predetermined torsion resisting the rotation of the pulleys 32 in a direction corresponding to the extension of the cords 24. Each of the clock springs 50 is housed within a corresponding spring sheath 52 that is fixed to the corresponding pulley 32. The drive shafts 34 are mounted to the internal frame 35 inside the outer housing 30 with mounting devices, shown as brackets 54. The pulleys 32 are rotatable relative to the corresponding drive shafts 34, which are connected to the internal frame 35. In various embodiments, the pulleys 32 are centrally located within the housing 30 such that the medial planes of the pulleys 32 are aligned with the medial plane of the internal frame 35.

Figure 9:
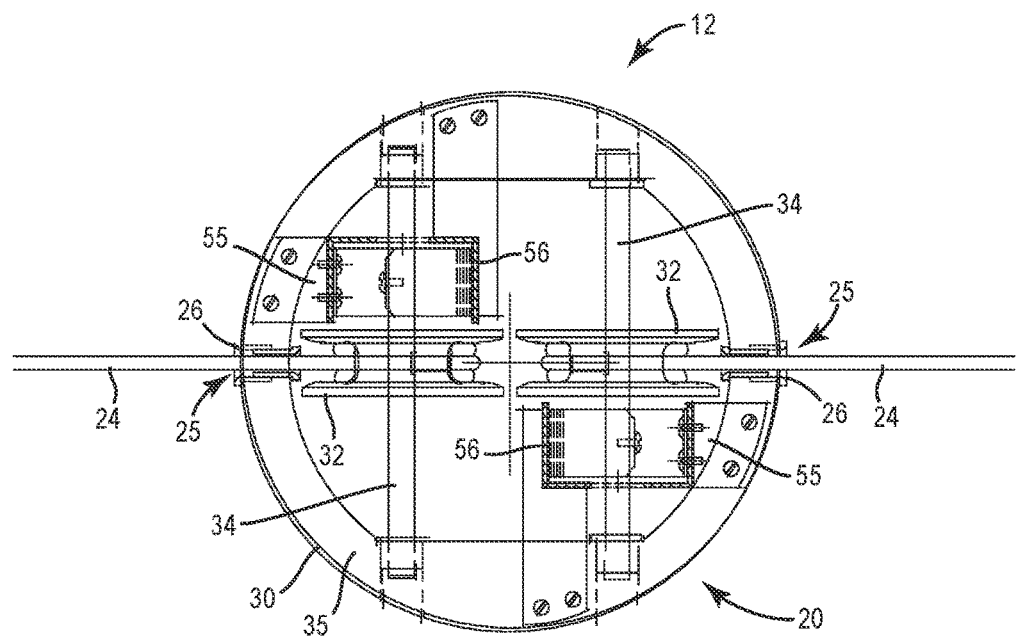
FIG. 9 is a top view of the interior of an exercise apparatus, according to an exemplary embodiment.

Referring now to FIG. 9, internal mechanisms of the exercise apparatus 12 are shown according to another exemplary embodiment. Each of the cords 24 extends through the outer housing 30 of the main body 20 through the corresponding opening 25 and engages the corresponding pulley 32. The pulleys 32 are coupled to parallel drive shafts 34, which are mounted to the internal frame 35 inside the outer housing 30. Tension is applied to the cords 24 via clock springs, which provide a constant, predetermined torsion resisting the rotation of the pulleys 32 in a direction corresponding to the extension of the cords 24. The clock springs are housed within spring sheaths 56 that are fixed to the internal frame 35 inside the outer housing 30 with mounting devices, shown as brackets 55. In various embodiments, the clock springs inside the spring sheaths 56 are coupled on one end to the internal frame 35 and on the other end to the drive shafts 34.

Figure 10:
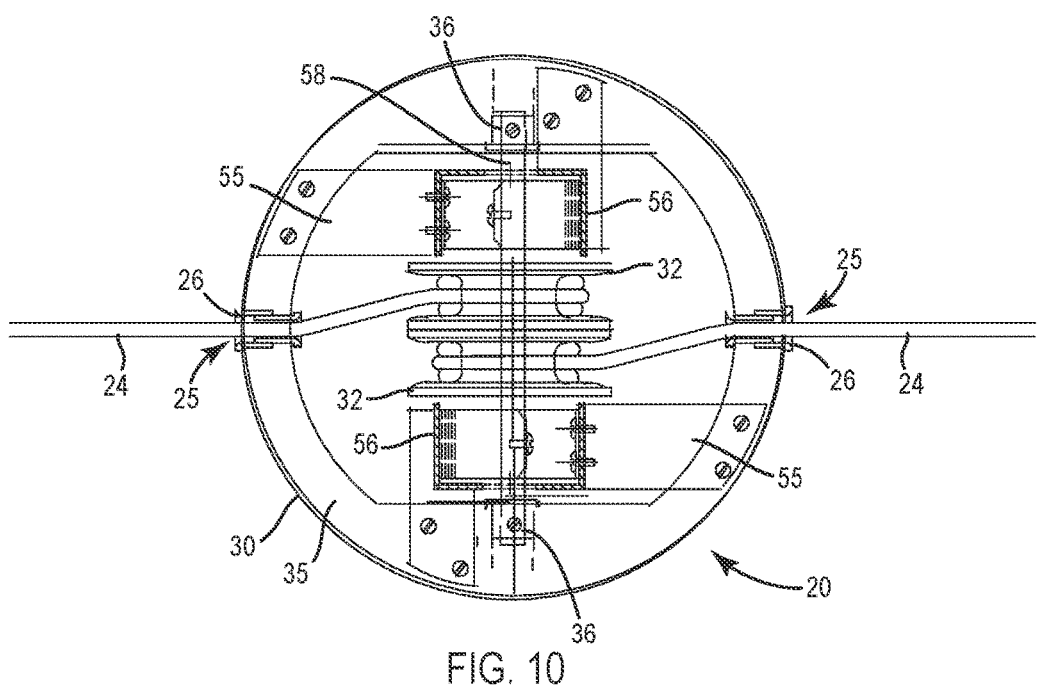
FIG. 10 is a top view of the interior of an exercise apparatus, according to an exemplary embodiment.

Referring now to FIG. 10, internal mechanisms of the exercise apparatus 12 are shown according to an exemplary embodiment. Each of the cords 24 extends through the outer housing 30 of the main body 20 through the corresponding opening 25 and engages the corresponding pulley 32. The pulleys 32 are coupled to a common drive shaft 58, which is connected to the internal frame 35 inside the outer housing 30. Bearings disposed between the pulleys 32 and the common drive shaft 58 allow the pulleys 32 to independently rotate relative to the common drive shaft 58. Tension is applied to the cords 24 via clock springs, which provide a constant, predetermined torsion resisting the rotation of the pulleys 32 in a direction corresponding to the extension of the cords 24. The clock springs are housed within the spring sheaths 56 that are fixed to the pulleys 32. In various embodiments, the clock springs are coupled on one end to the corresponding spring sheaths 56 and on the other end to the drive shaft 58. The drive shaft 58 is connected to the internal frame 35 with bearings 36.

Figure 11:
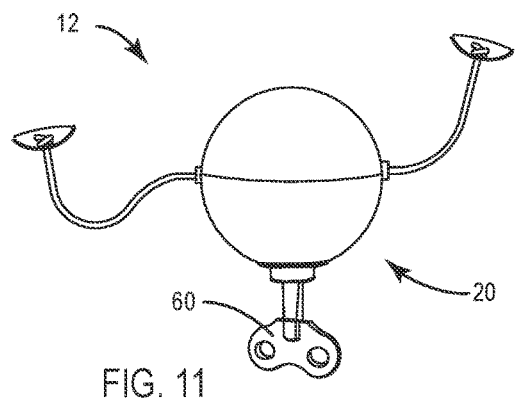
FIG. 11 is a front perspective view of an exercise apparatus, according to an exemplary embodiment.

Referring to FIG. 11, according to another exemplary embodiment, the exercise apparatus 12 includes a single handle 60 that is connected to a mechanism engaging both of the pulleys, such as the pulleys 32 in FIG. 5. With reference to FIGS. 5 and 11, in various embodiments, by turning the single handle 60, the user is able to adjust the resistance for both pulleys 32 simultaneously. The internal mechanism controlling the resistance on the pulleys may be similar to the mechanism describe above in regards to FIGS. 5 and 6, such that when the handle 60 is turned both foot members 44 apply further resistance to the corresponding pulleys 32, or may be another suitable mechanism.

Figure 12A:
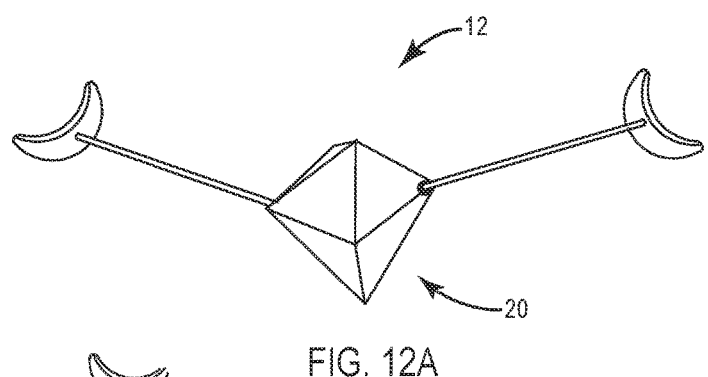
FIGS. 12A, 12B, and 12C are front perspective views of an exercise apparatus, according to exemplary embodiments.
Figure 12B:
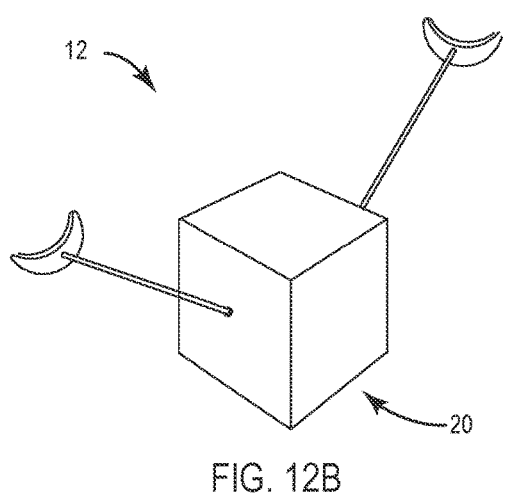
Figure 12C:
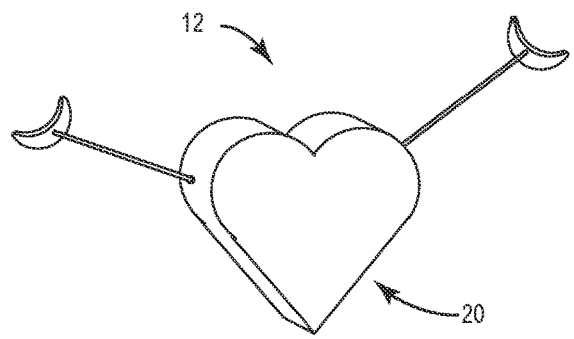
Figure 14:
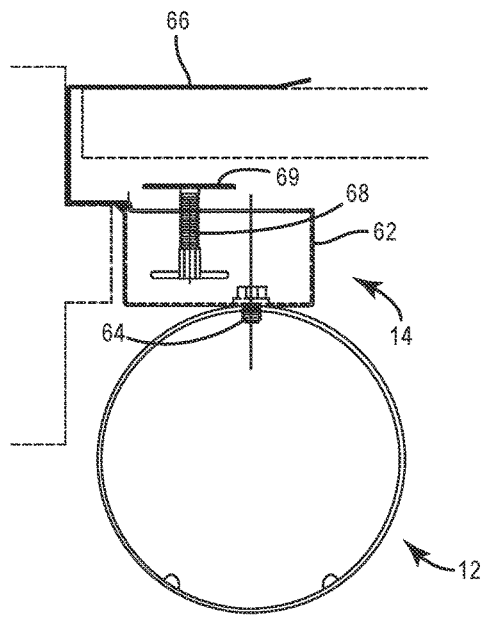
FIG. 14 is a top view of an exercise apparatus coupled to the mounting device of FIG. 13.
Figure 13:
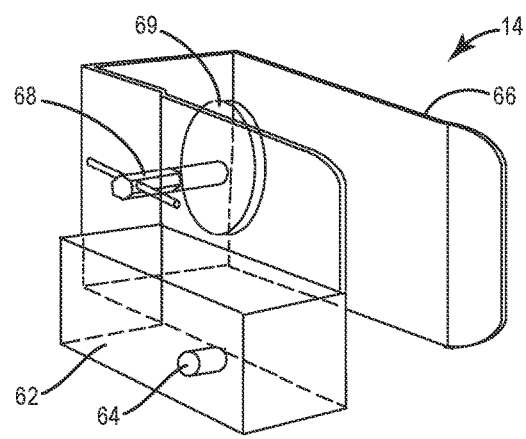
FIG. 13 is a front perspective view of a mounting device for an exercise apparatus, according to an exemplary embodiment.
Figure 15:
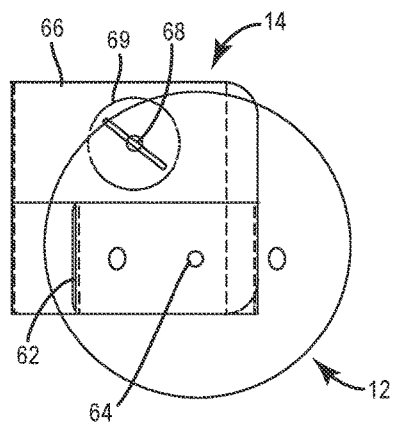
FIG. 15 is a front view of an exercise apparatus coupled to the mounting device of FIG. 13.
Figure 16:
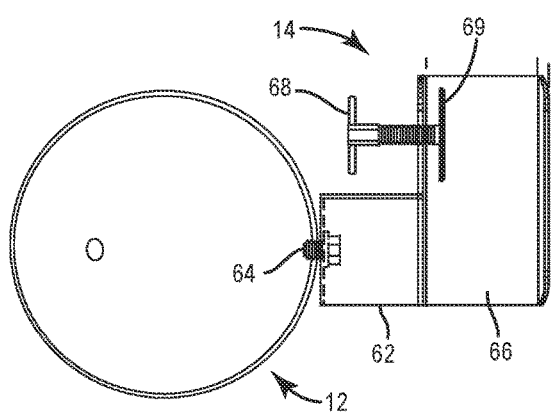
FIG. 16 is a side view of an exercise apparatus coupled to the mounting device of FIG. 13.

Referring to FIGS. 12A, 12B, and 12C, the main body 20 of the exercise apparatus 12 may be a shape other than a sphere in various embodiments. For example, the main body 20 may be oblong, shaped as a polyhedron, such as a cube, an octahedron, a dodecahedron, or the like, or shaped as a prism, such as a heart-shaped prism, or the like. In other embodiments, the main body 20 may be formed as any recognizable shape that appeals to the intended user. For example, an exercise apparatus intended for a child may have a main body 20 shaped like an animal, a cartoon character, a sports team logo, or the like.

Referring to FIGS. 13, 14, 15, and 16, the mounting device 14 for mounting the exercise apparatus 12 is shown according to an exemplary embodiment. The mounting device 14 includes a base 62, a first coupling member 64, shown as a threaded post, configured to be coupled to the exercise apparatus 12, and a second coupling member 66, shown as a c-shaped bracket, configured to be coupled to a stationary object. According to an exemplary embodiment, the second coupling member 66 is configured to engage a planar member, such as a door or a table. In various embodiments, the second coupling member 66 is shaped such that it is able to fit over an edge of a door or a table. The mounting device 14 is fixed in place relative to an object, such as a door or table, by tightening an adjustable member 68, shown as a thumb screw. Tightening the adjustable member 68 compresses the object between a wall of the second coupling member 66 and a disk 69, such as a plate, a platform, or the like, that is moved by the adjustable member 68. The second coupling member 66 is sized to allow the mounting device 14 to be coupled to most desks, tables, shelves, sills, or other similar interior or exterior surfaces.

In some embodiments, the adjustable member 68 and the first coupling member 64 are accessible by the user on the same side of the mounting device 14. In other embodiments, as described in more detail below, the adjustable member 68 and the first coupling member 64 are on opposite sides of the mounting device 14.

Figures 17, 18:
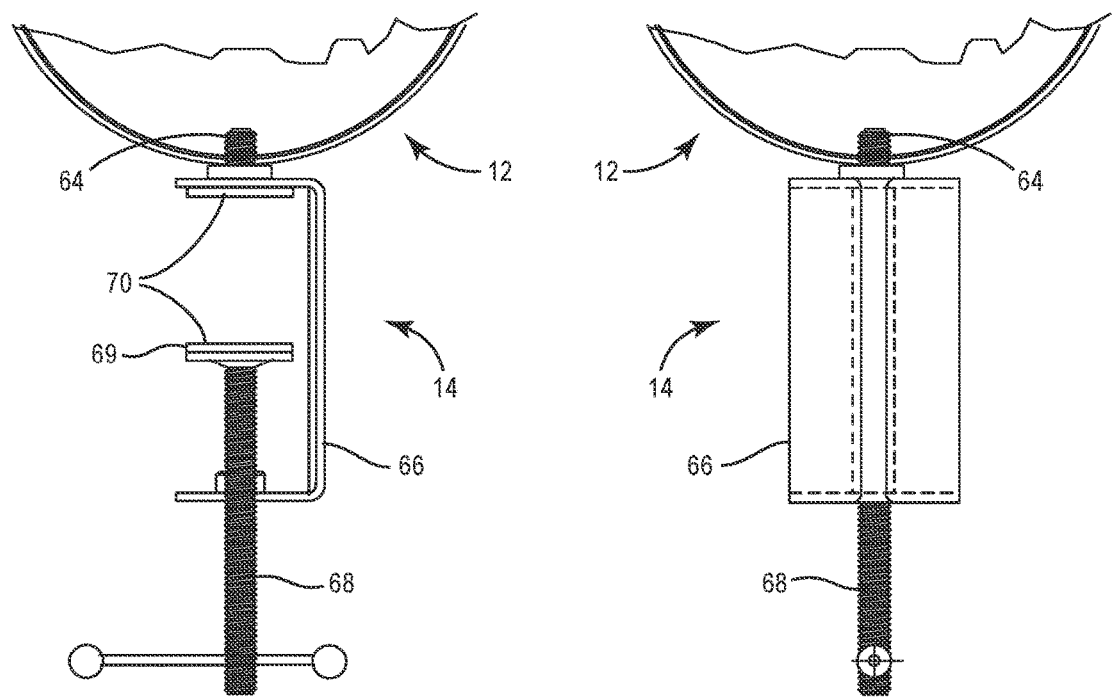
FIG. 17 is a side view of an exercise apparatus and mounting device, according to another exemplary embodiment.
FIG. 18 is a front view of the exercise apparatus and mounting device of FIG. 17.
Figure 19:
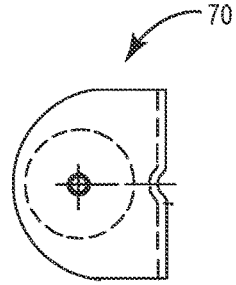
FIG. 19 is a front view of a clamp and resilient pad of the mounting device of FIG. 17.

Referring to FIGS. 17, 18, and 19, the mounting device 14 is shown according to another exemplary embodiment to include the adjustable member 68, shown as a thumb screw, disposed on an opposite side of the mounting device 14 from the first coupling member 64. One or more resilient pads 70 are provided on the inside surface of the second coupling member 66 and on the disk 69. The resilient pads 70 are formed from a compressible material, such as rubber, foam, cork, or the like, and are configured to protect the surfaces of the object to which the mounting device 14 is coupled. In various embodiments, the exercise apparatus 12 is connectable to the first coupling member 64, and an object such as a table or door is place between the disk 69 and the inside surface of the second coupling member 66, and the adjustable member 68 is rotatable to move the disk 69 to clamp the object between the disk 69 and the inside surface of the second coupling member 66, with the pads 70 protecting the object from scratches.

Figure 20:
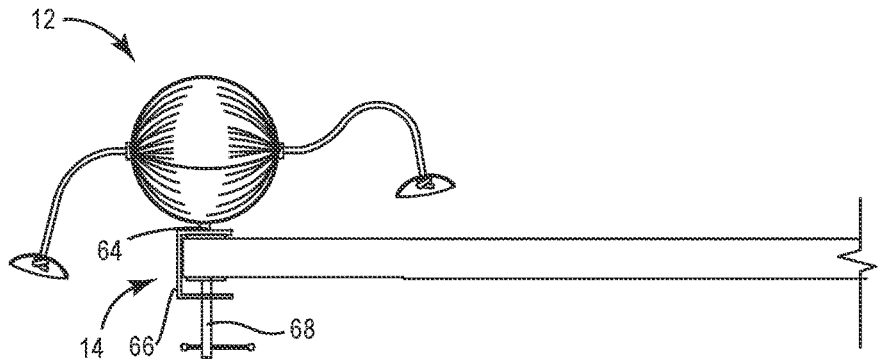
FIG. 20 is a side view of an exercise apparatus coupled to a table with the mounting device of FIG. 17, according to an exemplary embodiment.

Referring to FIG. 20, the exercise apparatus 12 is shown coupled to a table with the mounting device 14. The exercise apparatus 12 is disposed on the top of the table while the adjustable member 68 is disposed under the table, where it is unlikely to be inadvertently contacted by the user.

Figure 21:
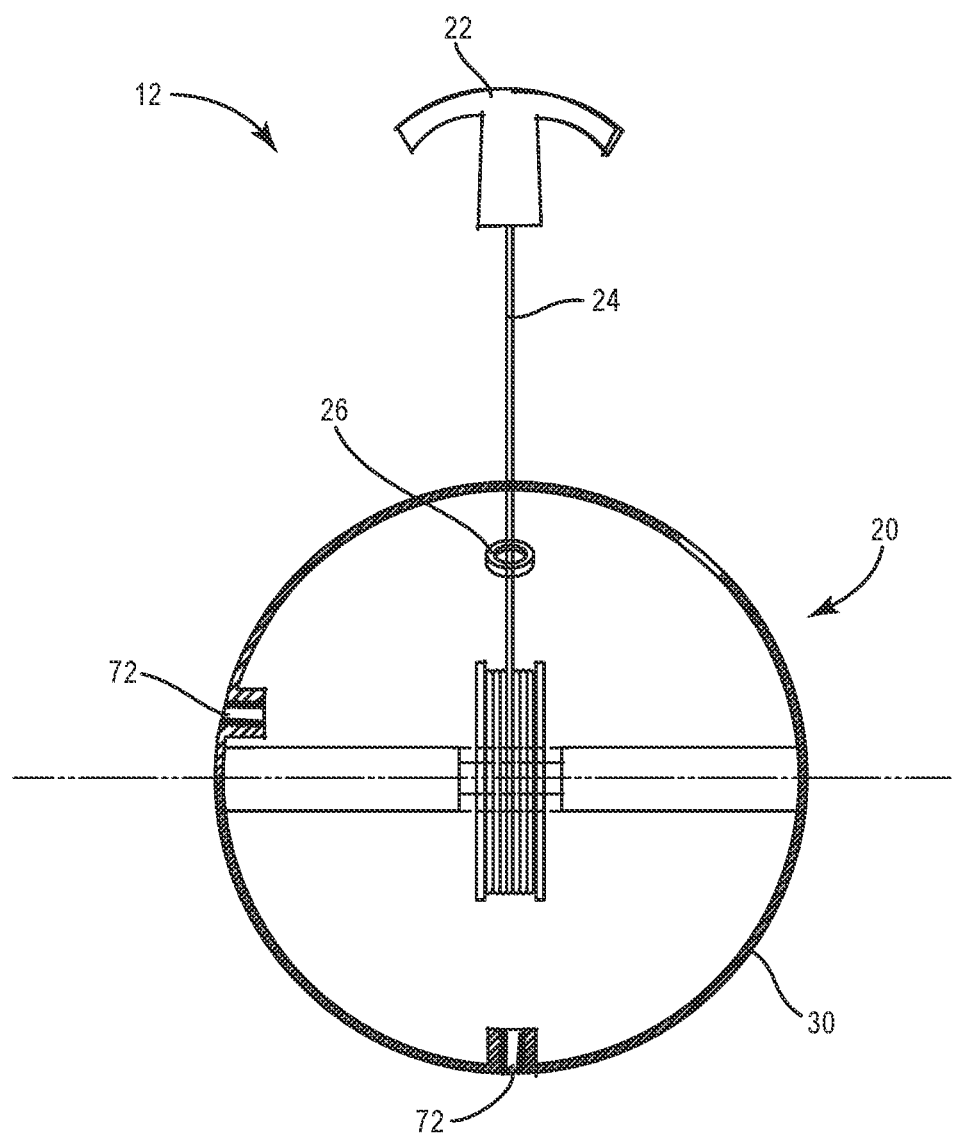
FIG. 21 is a cross-section view of an exercise apparatus, according to an exemplary embodiment.

Referring to FIG. 21, the exercise apparatus 12 in accordance with various embodiments includes one or more mounting features, shown as threaded openings 72 in the outer housing 30 of the main body 20. The threaded openings 72 are configured to directly or indirectly engage a coupling member of a mounting device, such as the first coupling member 64 of the mounting device 14 in FIG. 17.

Figure 22:
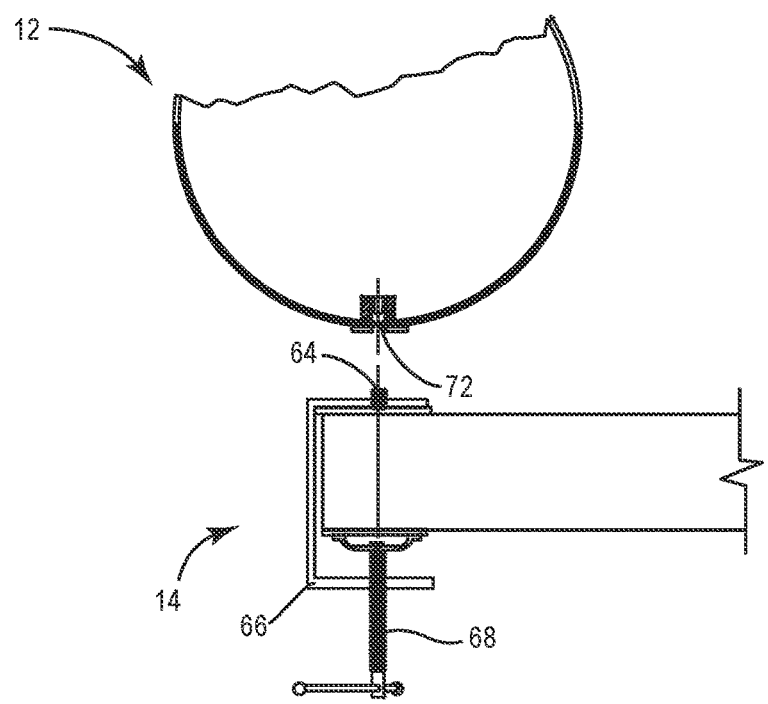
FIG. 22 is a side cross-section view of an exercise apparatus coupled to a table with a clamp mounting device, according to an exemplary embodiment.

Referring to FIG. 22, the exercise apparatus 12 is shown in accordance with an embodiment to be coupled to the mounting device 14 by threading one of the threaded openings 72 onto the first coupling member 64 of the mounting device 14.

Figure 23:
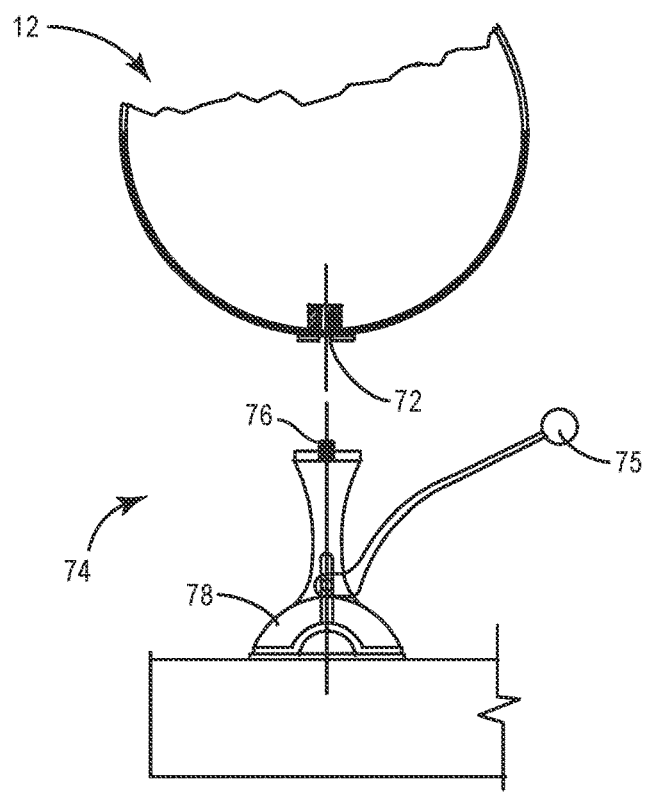
FIG. 23 is a side cross-section view of an exercise apparatus coupled to a table with a suction mounting device, according to an exemplary embodiment.

Referring to FIG. 23, the exercise apparatus 12 is shown in accordance with an embodiment to be coupled to another exemplary mounting device 74 by threading one of the threaded openings 72 onto a first coupling member 76 of the mounting device 74. The mounting device 74 is shown as a suction device that includes a second coupling member 78 in the form of a suction cup and an adjustable member in the form of a lever 75. The second coupling member 78 is configured to attach to an object, such as a table, and the lever 75 is connected to the second coupling member 78 to control the second coupling member 78.

Figure 24:
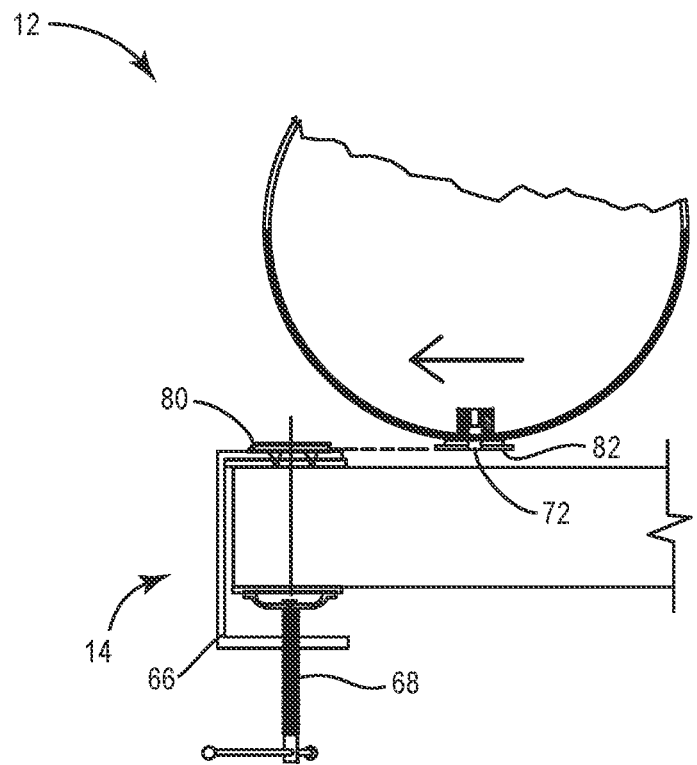
FIG. 24 is a side cross-section view of an exercise apparatus coupled to a table with a clamp mounting device, according to an exemplary embodiment.
Figure 25:
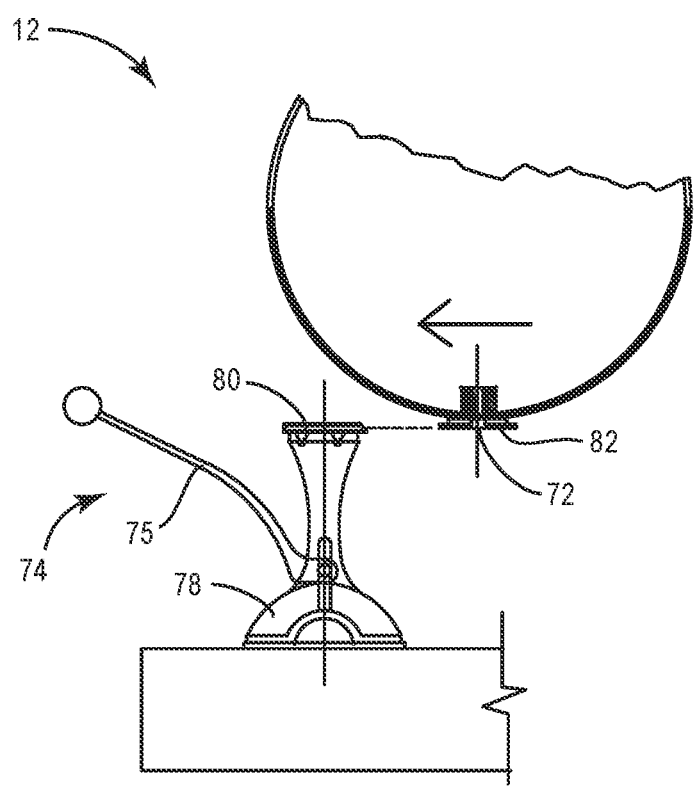
FIG. 25 is a side cross-section view of an exercise apparatus coupled to a table with a suction mounting device, according to an exemplary embodiment.

Referring to FIGS. 24 and 25, the exercise apparatus 12 is shown to be coupled to exemplary mounting devices 14 and 74, respectively, via a sliding clip connection in accordance with an embodiment. A first member 80 is coupled to the mounting device 14 or 74. A second member 82 is coupled to the threaded opening 72 in the exercise apparatus 12. The second member 82 engages the first member 80 with a sliding connection to allow the exercise apparatus 12 to be easily coupled to and decoupled from the mounting device 14 or 74.

Figure 26:
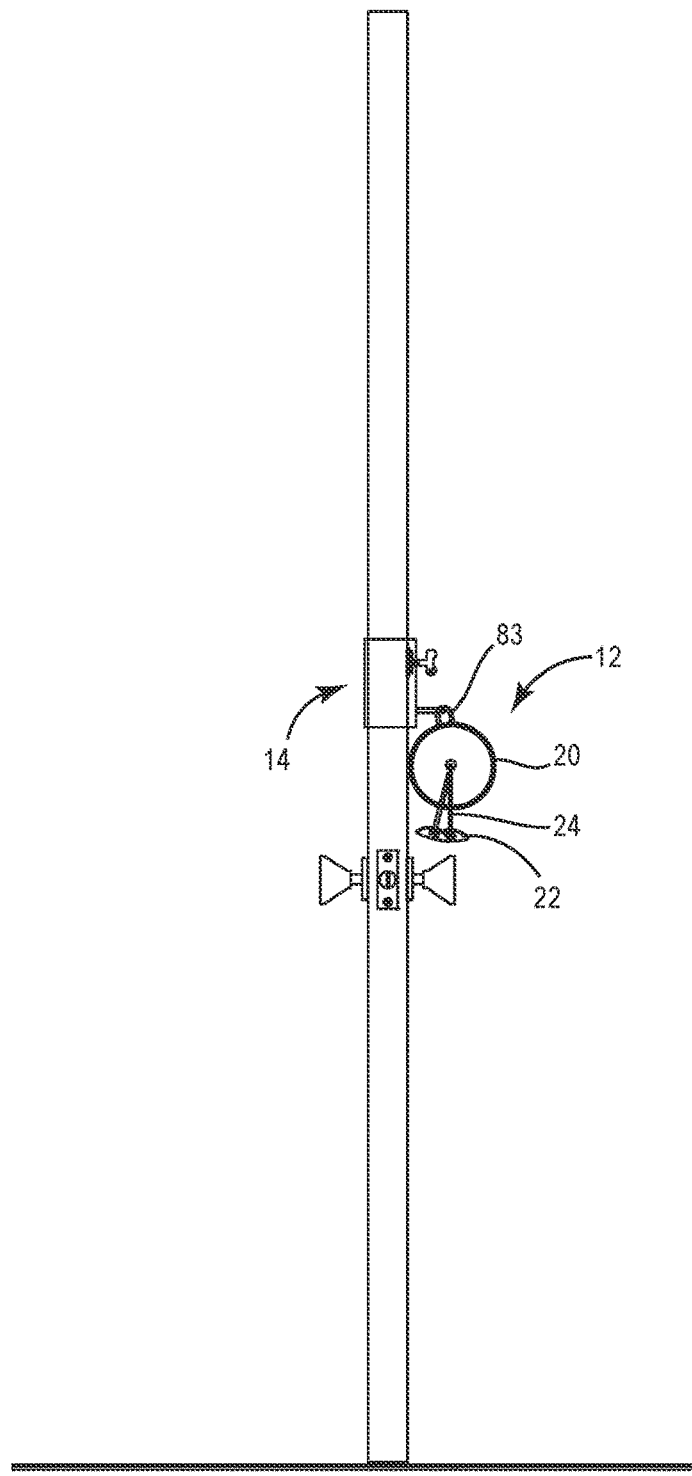
FIG. 26 is a side view of an exercise apparatus coupled to a door with a mounting device, according to an exemplary embodiment.

Referring to FIG. 26, the exercise apparatus 12 is shown in accordance with an embodiment as coupled to a door with the mounting device 14. In various embodiments, the mounting device 14 is coupled to the edge of a door anywhere along the height of the door. For example, while the mounting device 14 is shown above the door knob, in other embodiments, the mounting device 14 can be disposed above or below the door knob at any height depending on the height and position (e.g., standing, sitting, laying down, etc.) of the user. In one embodiment, the exercise apparatus 12 is coupled to the mounting device 14 with a hasp 83 that allows the exercise apparatus 12 to move relative to the mounting device 14.

Figure 27:
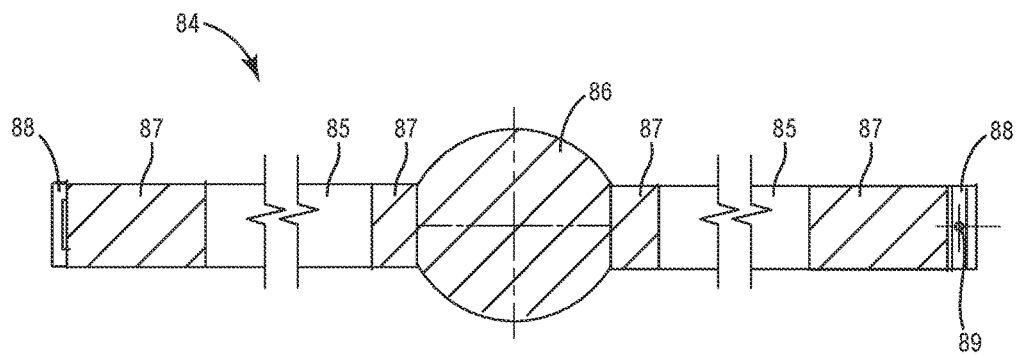
FIG. 27 is a front view of a belt mounting device for an exercise apparatus, according to an exemplary embodiment.

Referring to FIG. 27, a mounting device is shown according to another exemplary embodiment as a belt mounting device 84. In various embodiments, the belt mounting device 84 includes flexible portions 85 formed form flexible materials, such as an elastic or the like, and also includes non-flexible portions 87 formed from non-flexible materials, such as fabric, leather, or the like. In some embodiments, the belt mounting device 84 is provided in different base lengths to accommodate users with different waist sizes. In various embodiments, the belt mounting device 84 includes a padded, enlarged portion 86. The enlarged portion 86 is configured to be positioned at the spine of the user to provide additional back support and to improve posture. The free ends of the belt mounting device 84 are able to be coupled together with interlocking clasps 88. One or both of the clasps 88 define an opening 89. In some embodiments, the belt mounting device 84 is utilized with suspenders having an adjustable length to allow the user to better position the belt mounting device 84 to provide improved support and comfort to the user.

Figure 28:
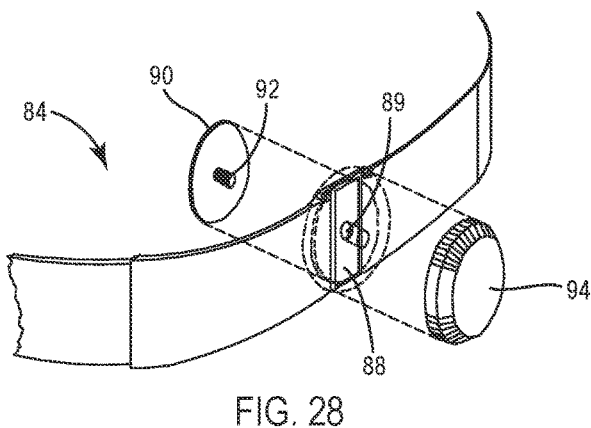
FIG. 28 is a perspective view of a belt mounting device of FIG. 27, according to an exemplary embodiment.

Referring to FIG. 28, in some embodiments a disk 90 having a threaded post 92 is coupled to the belt mounting device 84. The disk 90 is positioned on the inside of the belt mounting device 84 proximate to the clasps 88, and the threaded post 92 is inserted through the opening 89. The exercise apparatus 12 is then mounted to the threaded post 92 via one of the threaded openings 72 in the exercise apparatus 12 (refer to FIG. 21). In some embodiments, a cap 94 is provided to be coupled to the threaded post 92 when the exercise apparatus 12 is removed from the threaded post 92. In some embodiments, the cap 94 includes a graphic, logo, or other indicia.

Figures 29, 30:
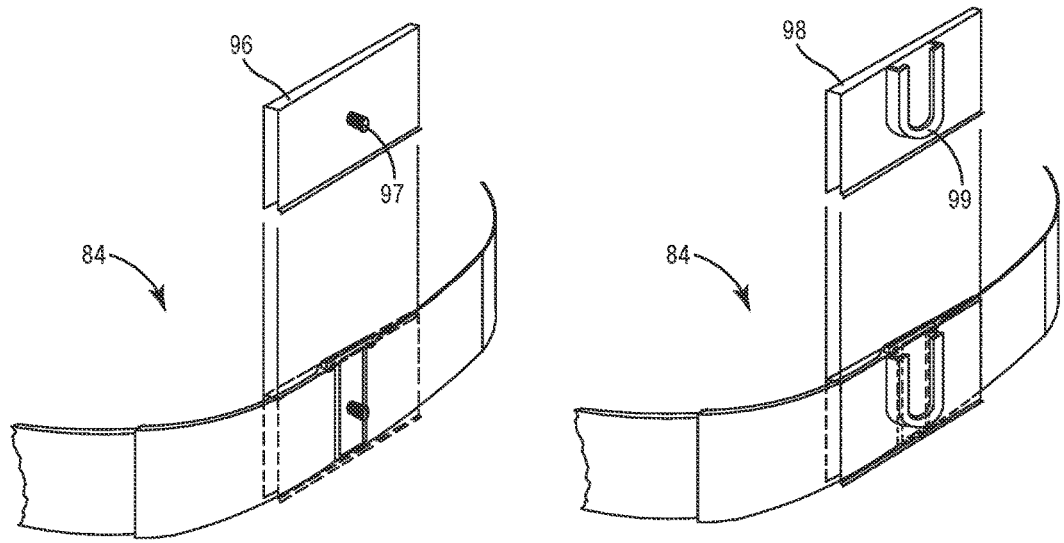
FIG. 29 is a perspective view of a belt mounting device of FIG. 27, according to another exemplary embodiment.
FIG. 30 is a perspective view of a belt mounting device of FIG. 27, according to another exemplary embodiment.

Referring to FIG. 29, in some embodiments a clip 96 having a threaded post 97 is coupled to the belt mounting device 84. The clip 96 is able to slide over the belt mounting device 84. The exercise apparatus 12 is then able to be mounted to the threaded post 97 via one of the threaded openings 72 in the exercise apparatus 12 (refer to FIG. 21).

Referring to FIG. 30, in some embodiments a clip 98 having a U-shaped receptacle 99 is coupled to the belt mounting device 84. The clip 98 is able to slide over the belt mounting device 84. The exercise apparatus 12 (refer to FIG. 1) is then mounted to the U-shaped receptacle 99 with a sliding connection, similar to the connection between the members 80 and 82 shown in FIGS. 24 and 25.

Figure 31:
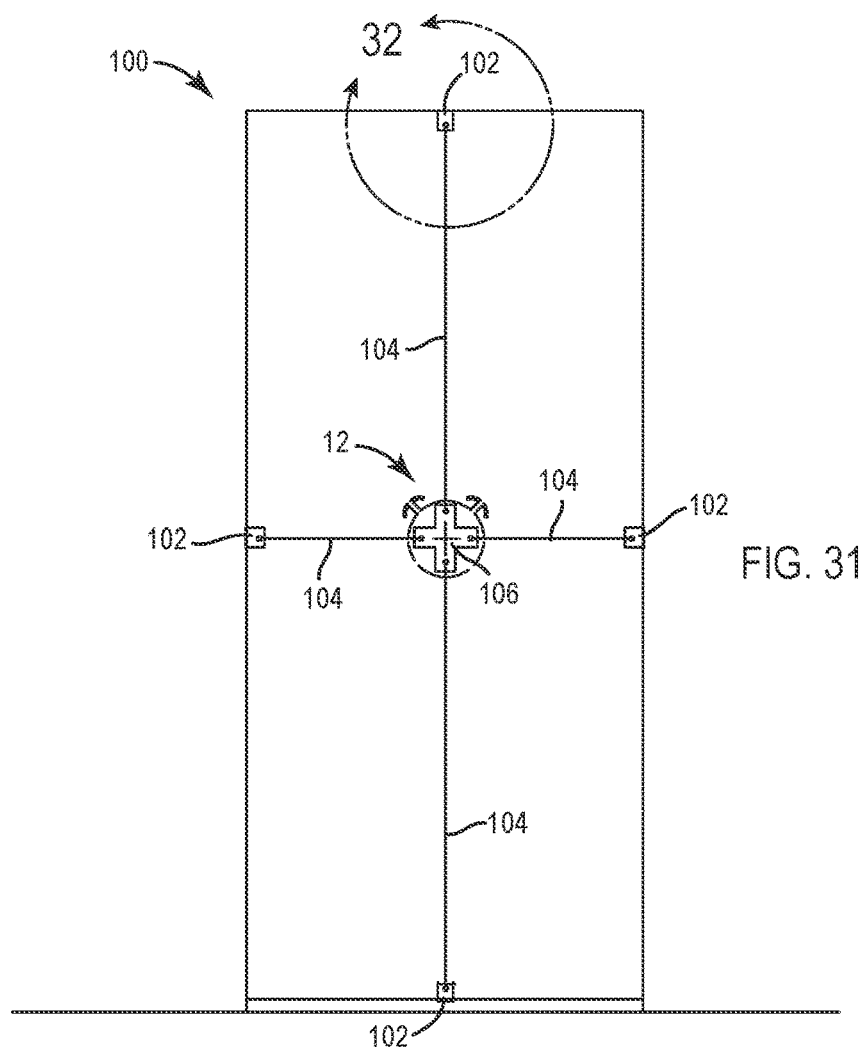
FIG. 31 is a front view of an exercise apparatus coupled to a door with a mounting device, according to an exemplary embodiment.
Figure 32:
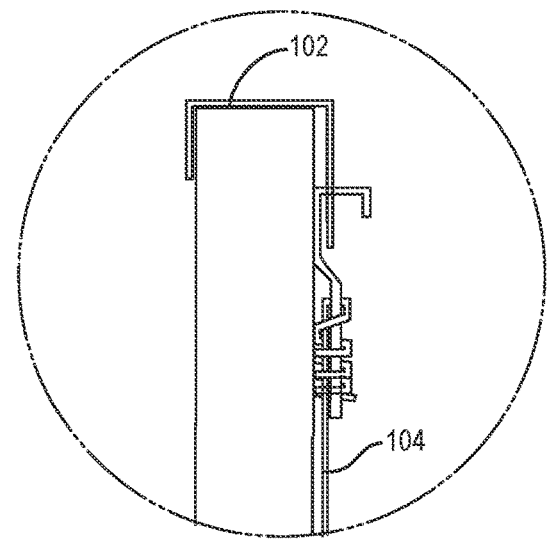
FIG. 32 is a side view of a portion of the mounting device of FIG. 31.

Referring to FIGS. 31 and 32, a mounting device 100 is shown according to another exemplary embodiment. The mounting device 100 includes a multitude of clips 102 that are configured to engage the edges of a relatively flat base member, such as a door. The clips 102 are coupled to a central mount 106 via cords 104. According to an exemplary embodiment, the cords 104 are flexible members, such as elastic or the like, allowing the mounting device 100 to be utilized with a door or other object of different sizes. The exercise apparatus 12 is coupled to the central mount 106, such as via a threaded connection, a sliding connection, or the like. According to an exemplary embodiment, the mounting device 100 includes four clips 102, with each clip 102 engaging an edge of a rectangular door. In this way, the mounting device 100 provides both horizontal and vertical support to the exercise apparatus 12. In another embodiment, the mounting device 100 includes more than four clips 102. In yet another embodiment, the mounting device 100 includes only two clips 102 and provides only vertical support to the exercise apparatus 12. According to an exemplary embodiment, the mount 106 is located approximately centrally on the door. In other embodiments, the mount 106 may be located off-center on the door or other stationary object.

Figure 33A:
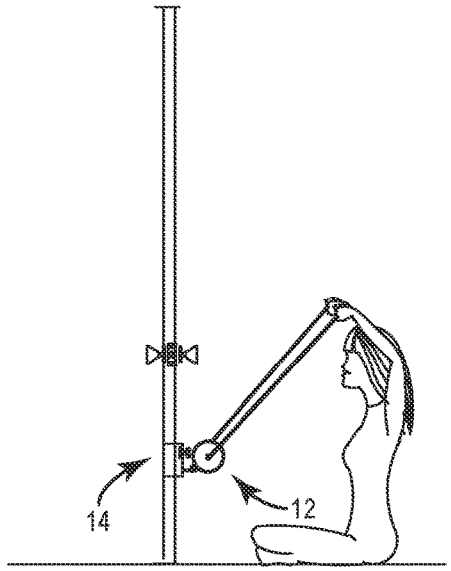
FIGS. 33A, 33B, 33C, and 33D are side views of an exercise apparatus coupled to a door with a mounting device, being used by a user in several configurations according to various methods.
Figure 33B:
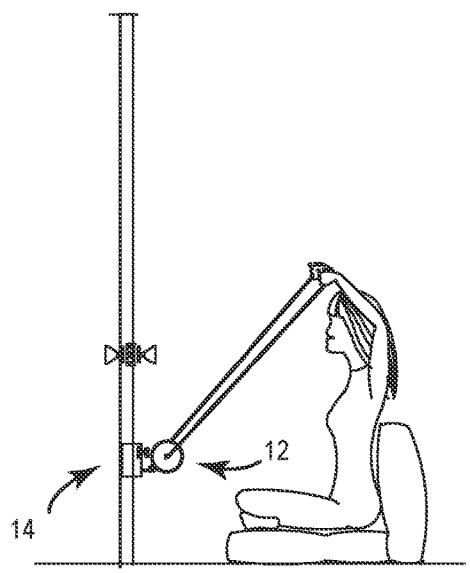
Figure 33C:
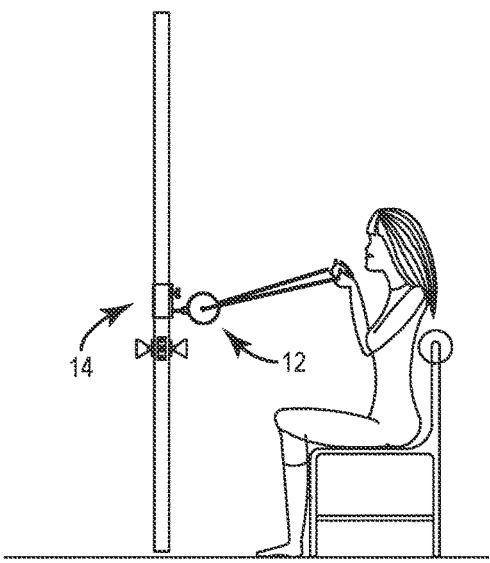
Figure 33D:
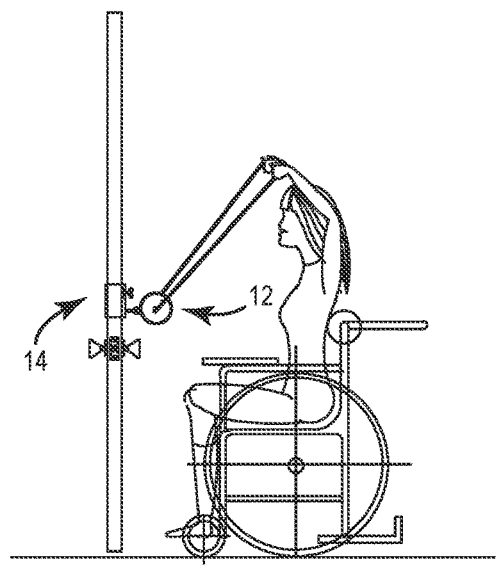

Referring to FIGS. 33A, 33B, 33C, and 33D, a user is shown interacting with the exercise apparatus 12 while in a variety of positions. FIG. 33A shows a user interacting with the exercise apparatus 12 while seated on the floor. FIG. 33B shows a user interacting with the exercise apparatus 12 while seated on a pillow on the floor. FIG. 33C shows a user interacting with the exercise apparatus 12 while seated on a chair. FIG. 33D shows a user interacting with the exercise apparatus 12 while seated in a wheelchair. As shown by FIGS. 33A, 33B, 33C, and 33D, the mounting device 14 is able to be positioned at different positions on a door to accommodate the different sitting positions of the user.

Figure 34A:
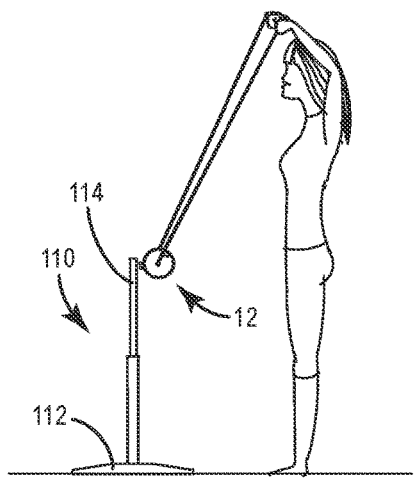
FIGS. 34A and 34B are side views of an exercise apparatus coupled to a stand, being used by a user in several configurations according to various methods.
Figure 34B:
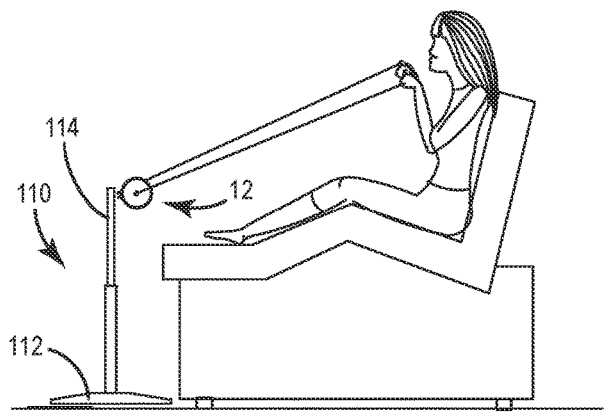

Referring to FIGS. 34A and 34B, the exercise apparatus 12 is shown coupled to a stand 110. The stand 110 includes a relatively wide base 112 and a column 114 to which the exercise apparatus 12 is coupled. In some embodiments, the column 114 is a telescoping member to allow the exercise apparatus 12 to be positioned at a variety of heights. FIG. 34A shows a user interacting with the exercise apparatus 12 on the stand 110 while in a standing position. FIG. 34B shows a user interacting with the exercise apparatus 12 on the stand 110 while in a reclining position, such as while in a hospital bed.

Figure 35:
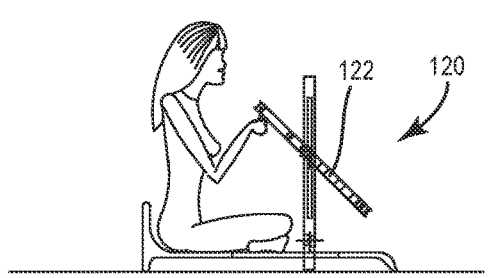
FIG. 35 is a side view of an exercise apparatus coupled to a guide, according to an exemplary embodiment.
Figure 36:
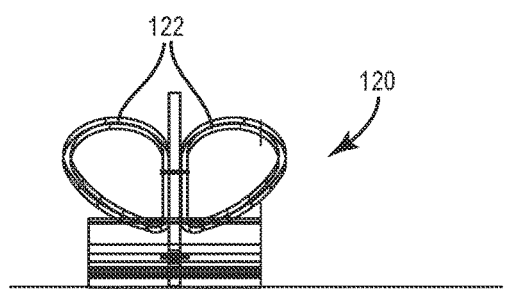
FIG. 36 is a front view of the guide of FIG. 35.
Figure 37A:
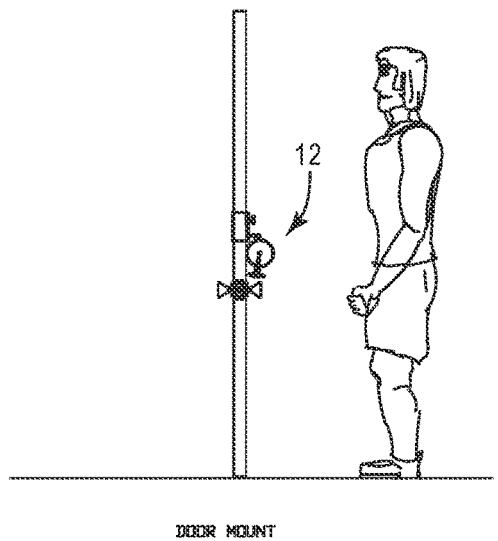
FIGS. 37A, 37B, 37C, 37D, 37E, 37F, 37G, and 37H are views of a user using an exercise apparatus, according to an exemplary embodiment.
Figure 37B:
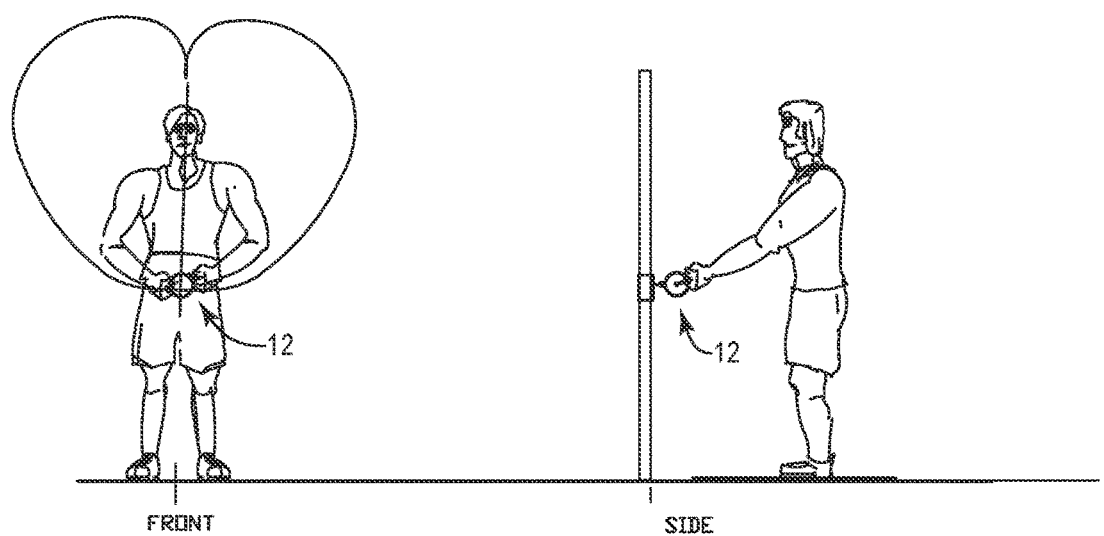
Figure 37C:
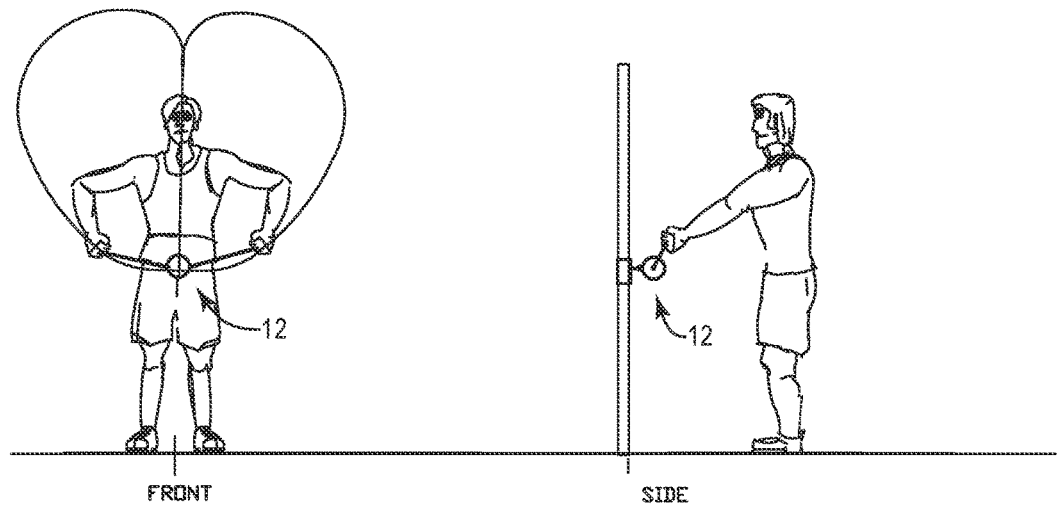
Figure 37D:
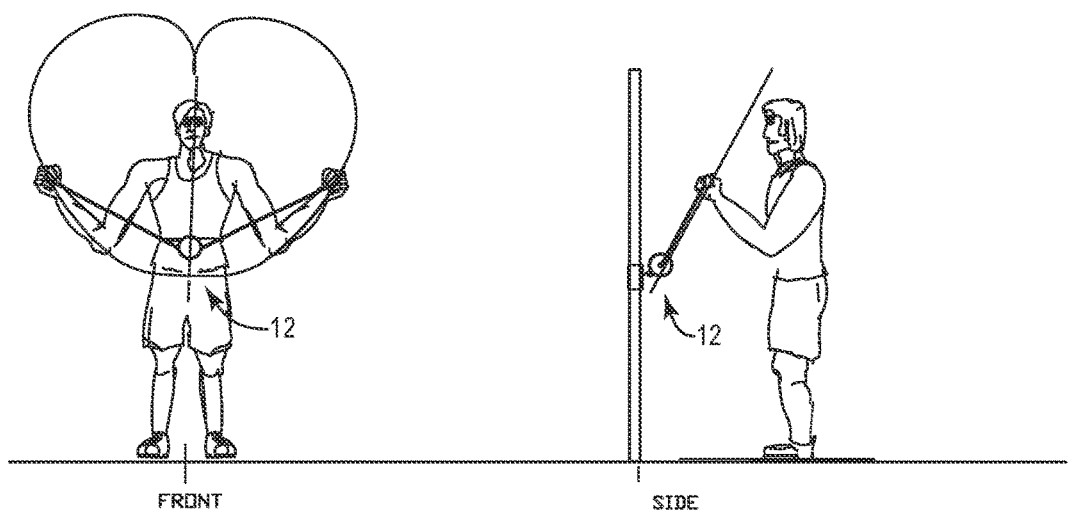
Figure 37E:
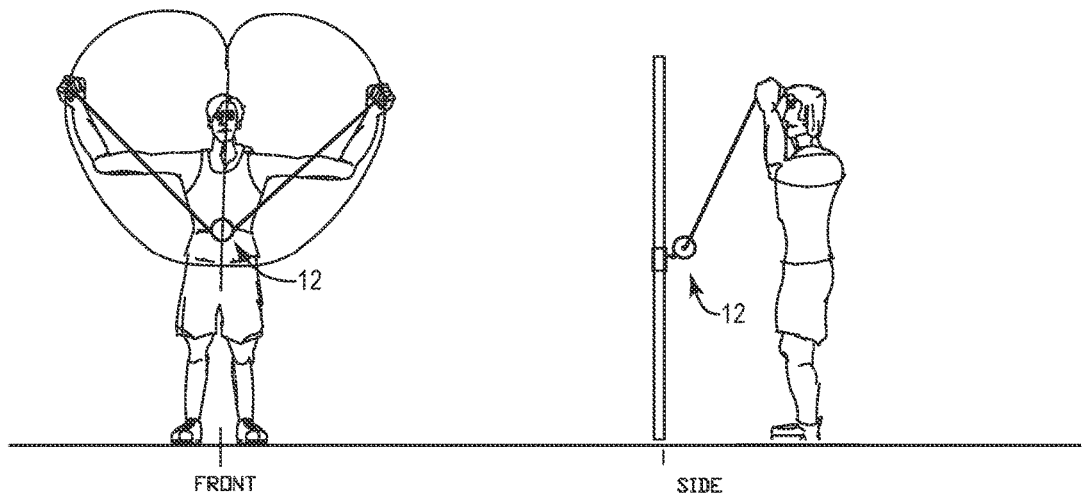
Figure 37F:
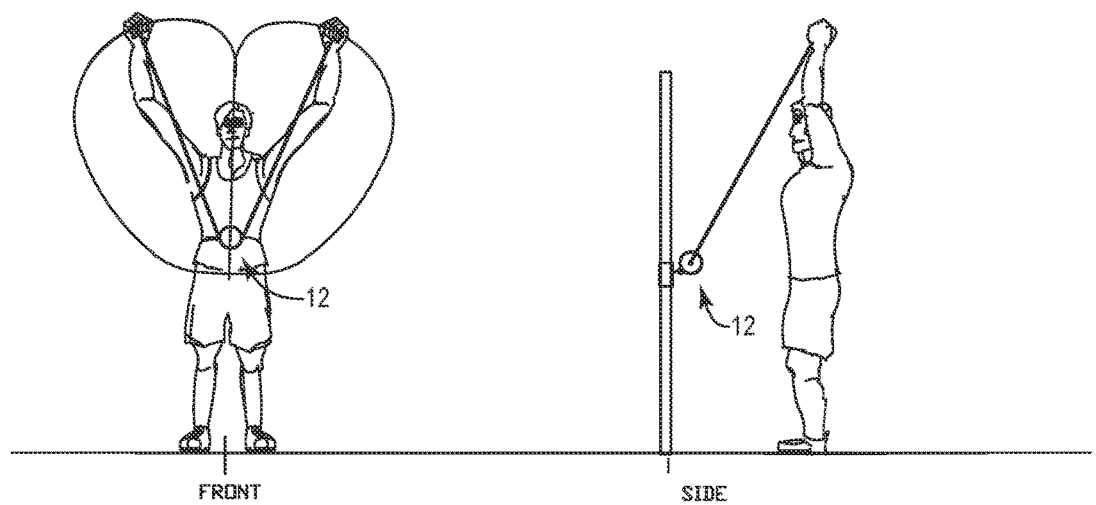
Figure 37G:
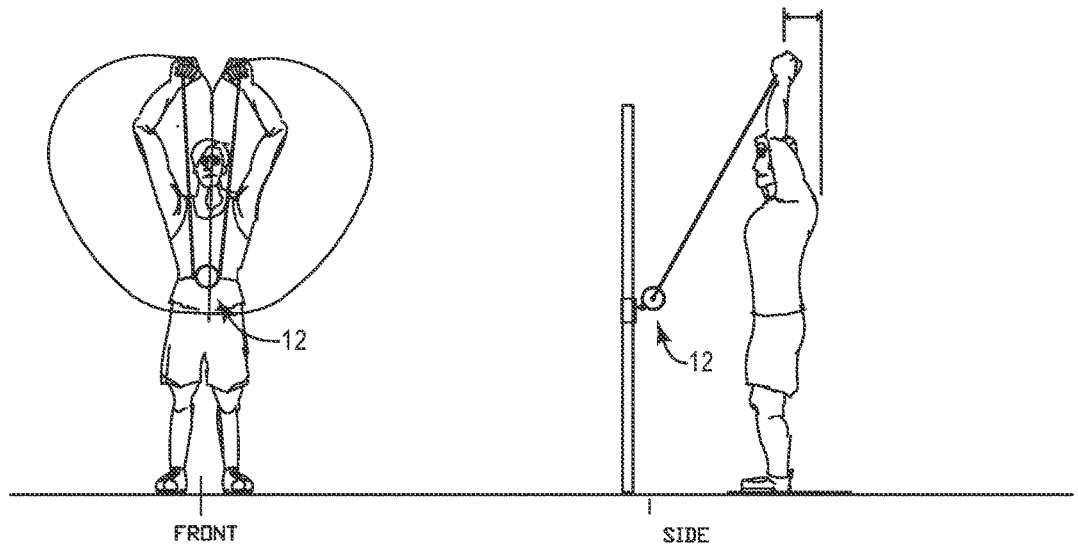
Figure 37H:
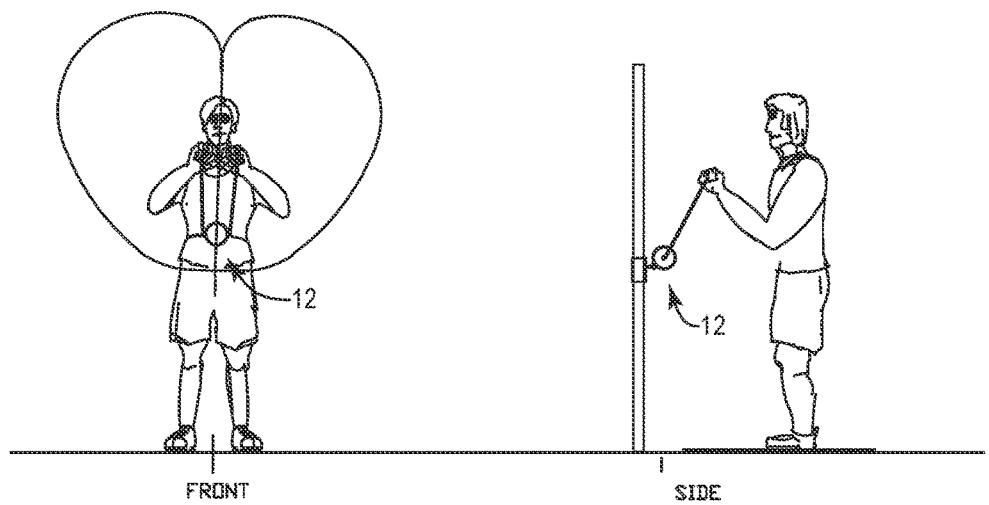

Referring to FIGS. 35 and 36, an exercise apparatus 120 is shown with adjustable guide tracks 122 and handles. In various embodiments, the guide tracks 122 guide the movement of the user in a predetermined pattern of motion while using the exercise apparatus 120.

Referring to FIGS. 37A, 37B, 37C, 37D, 37E, 37F, 37G, and 37H, steps in a method in accordance with an embodiment of a user completing an exemplary aided respiration cycle using the exercise apparatus 12 of FIG. 1 are shown. The method will now be described with reference to FIGS. 1, 37A, 37B, 37C, 37D, 37E, 37F, 37G, and 37H. The mounting device 14 is first coupled to a stationary body, such as a table or door. The exercise apparatus 12 is then coupled to the mounting device 14 such that the main body 20 of the exercise apparatus 12 is held relatively stationary (see FIG. 37A). The user may then exercise with several unique routines that accommodate users of various abilities, sizes, and strengths. In some embodiments, the user grasps the handles 22 and moves their hands in a roughly heart-shaped pattern. In some embodiments, the heart shaped pattern is facilitated by a pair of curved bards that the user may follow. The user first grips the handles 22 as shown in front and side views in FIG. 37B. The user then moves their hands upward and outward. As the user moves their hands, the cords 24 exert a constant tension which guides the user in following a learned path of travel for the routine as shown in the front and side views in FIG. 37C. As the user moves their hands upward, the movement causes the arms to extend outward and the shoulders to move backwards, allowing the user's diaphragm to begin to expand and the angle of the back and spine to rise as shown in the front and side views in FIG. 37D. As the user's arms approach the zenith of the heart-shaped pattern and each of the cords moves in an arc pattern, the shoulders are positioned correctly and the user's lungs can now inhale and exhale most beneficially as shown in front and side views in FIG. 37E. Continued repetitions of this motion teach the user to adopt this posture in order to maximize the healthful, therapeutic experience. As the arms extend to the horizontal limits of the heart shape, resistance tension on the cords 24 allows the user to test their ability to exert pressure in the outward and upward direction as shown in the front and side views in FIG. 37F. The upper position of the arms follow the outline of the heart shape, thereby greatly improving posture of the upper body. In the upper position, oxygen to the lungs is expanded, improving body alignment and creating length and space to the body. Improvement to exhalation of carbon dioxide function is further enhanced. The user may then return the arms down as the cords 24 are retracted as shown in the front and side views in both FIG. 37G and FIG. 37H. Continued repetitions of this exercise, followed by periods of rest, can improve breathing, blood flow, posture, and a general feeling of invigoration for the user.

A method for using an exercise apparatus in accordance with an embodiment includes moving an adjustment mechanism to adjust a pull-out tension provided by a first cord of the exercise apparatus independently of a retraction tension provided by the first cord. The pull-out tension is a tension provided by the first cord when the first cord is pulled from a first pulley, and the retraction tension is a tension provided by the first cord when the first cord is retracted around the first pulley. In various embodiments, the method further includes pulling the first cord and a second cord of the exercise apparatus at a same time and each in an arc motion. In some embodiments, the method further includes attaching the exercise apparatus to a door using a plurality of clips that slide on the door.

The terms "coupled," "connected," "attached," and the like as used herein mean the joining of two members directly or indirectly to one another. Such joining may be stationary (e.g., permanent) or moveable (e.g., removable, releasable, rotatable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

The construction and arrangement of the elements of the exercise apparatus and mounting device as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments as various modifications may be made in various different embodiments. It should be noted that the elements and/or assemblies may be constructed from any of a wide variety of materials that provide sufficient strength or durability, in any of a wide variety of colors, textures, and combinations.

What is claimed is:

1. An exercise apparatus, comprising:
a first cord that is pullable from and retractable around a first pulley;
a second cord that is pullable from and retractable around a second pulley; and
an adjustment mechanism for adjusting a pull-out tension provided by the first cord independently of a retraction tension provided by the first cord;
wherein the adjustment mechanism comprises a member with opposing sides that are curved to a tip that is positionable to apply resistance to an outside circumference of the first pulley; and
wherein the pull-out tension is a tension provided by the first cord when the first cord is pulled from the first pulley, and the retraction tension is a tension provided by the first cord when the first cord is retracted around the first pulley.

2. The exercise apparatus of claim 1,
wherein the member of the adjustment mechanism has an asymmetrical shape in which the opposing sides of the member are curved differently from each other to provide a resistance against movement of the first pulley when the first pulley rotates in a first direction and to permit movement of the first pulley when the first pulley rotates in an opposite direction from the first direction.

3. The exercise apparatus of claim 2,
wherein the first pulley is configured to rotate in the first direction when the first cord is pulled from the first pulley, and is configured to rotate in the opposite direction when the first cord is retracted around the first pulley.

4. The exercise apparatus of claim 1, further comprising:
a second adjustment mechanism for adjusting a pull-out tension provided by the second cord independently of a retraction tension provided by the second cord; and
a main body that is a hollow sphere for housing the first pulley and the second pulley, the hollow sphere including a first opening through which the first cord is moveable and a second opening through which the second cord is moveable;
wherein the second adjustment mechanism includes a threaded rod that extends through a third opening in the hollow sphere;
wherein the first opening, the second opening, and the third opening in the hollow sphere are all entirely located in a same hemisphere of the hollow sphere as each other; and
wherein the pull-out tension provided by the second cord is a tension provided by the second cord when the second cord is pulled from the second pulley, and the retraction tension provided by the second cord is a tension provided by the second cord when the second cord is retracted around the second pulley.

5. The exercise apparatus of claim 1,
wherein the adjustment mechanism includes a knob for adjusting a resistance to be applied to the first pulley against rotation of the first pulley in a first direction independent of any adjustment of freedom of movement of the first pulley in an opposite direction from the first direction;
wherein the adjustment mechanism includes a threaded rod attached to the knob that is rotatable to position the member of the adjustment mechanism; and
wherein the adjustment mechanism includes a pin that extends through an opening in the member of the adjustment mechanism in a direction that is perpendicular to a direction that the threaded rod extends from the knob.

6. The exercise apparatus of claim 1, further comprising:
a shaft;
wherein the first pulley and the second pulley are both positioned around the shaft.

7. The exercise apparatus of claim 1, further comprising:
a first shaft; and
a second shaft separate from the first shaft;
wherein the first pulley is positioned around the first shaft, and the second pulley is positioned around the second shaft;
wherein the adjustment mechanism includes a threaded rod connected to a knob that is rotatable to position the member of the adjustment mechanism; and
wherein the threaded rod extends from the knob in a different direction than a direction in which the first shaft extends through the first pulley.

8. The exercise apparatus of claim 1, further comprising:
a main body for housing the first pulley and the second pulley, the main body including a first opening through which the first cord is moveable and a second opening through which the second cord is moveable.

9. The exercise apparatus of claim 8,
wherein the main body is in the shape of a hollow sphere, and the first opening is an opening in an outer surface of the hollow sphere, and the first opening is on an opposite side of the hollow sphere from the second opening.

10. The exercise apparatus of claim 8,
wherein the main body is in the shape of a sphere and the first opening is entirely within a same hemisphere of the sphere as the second opening.

11. The exercise apparatus of 8,
wherein the main body further includes a threaded opening for attachment of the main body to a mounting device.

12. The exercise apparatus of claim 1, further comprising:
a first handle attached to the first cord; and
a second handle attached to the second cord.

13. An exercise apparatus assembly, comprising:
an exercise apparatus, comprising:
a first cord that is pullable from and retractable around a first pulley;

a second cord that is pullable from and retractable around a second pulley; and an adjustment mechanism for adjusting a pull-out tension provided by the first cord independently of a retraction tension provided by the first cord, wherein the adjustment mechanism comprises a member with opposing sides that are curved to a tip that is positionable to apply resistance to an outside circumference of the first pulley, and wherein the pull-out tension is a tension provided by the first cord when the first cord is pulled from the first pulley, and the retraction tension is a tension provided by the first cord when the first cord is retracted around the first pulley; and a mounting device;

wherein the exercise apparatus is configured such that the exercise apparatus is mountable on and removable from the mounting device.

14. The exercise apparatus assembly of claim 13, wherein the mounting device includes a first coupling member for connecting the exercise apparatus to the mounting device and a second coupling member for mounting the mounting device on an object.

15. The exercise apparatus assembly of claim 14, wherein the mounting device further includes an adjustment member that is moveable to hold the object between the adjustment member and the second coupling member.

16. The exercise apparatus assembly of claim 15, wherein the adjustment member is located on air opposite side of the second coupling member from the first coupling member.

17. The exercise apparatus assembly of claim 13, wherein the mounting device comprises a belt for wearing by a user.

18. The exercise apparatus assembly of claim 13, wherein the mounting device comprises a suction cup for providing suction to an object.

19. An exercise apparatus assembly, comprising:

an exercise apparatus, comprising:

a first cord that is pullable from and retractable around a first pulley;

a second cord that is pullable from and retractable around a second pulley; and an adjustment mechanism for adjusting a pull-out tension provided by the first cord independently of a retraction tension provided by the first cord, wherein the adjustment mechanism comprises a member with opposing sides that are curved to a tip that is positionable to apply resistance to an outside circumference of the first pulley, and wherein the pull-out tension is a tension provided by the first cord when the first cord is pulled from the first pulley, and the retraction tension is a tension provided by the first cord when the first cord is retracted around the first pulley; and a clip that is slidable over a belt and upon which the exercise apparatus is mountable.

20. The exercise apparatus assembly of claim 19, wherein the clip includes a U-shaped receptacle.

* * * * *